United States Patent
Rao et al.

(10) Patent No.: US 7,863,012 B2
(45) Date of Patent: Jan. 4, 2011

(54) ANALYSIS OF CIRCULATING TUMOR CELLS, FRAGMENTS, AND DEBRIS

(75) Inventors: Galla Chandra Rao, Princeton Junction, NJ (US); Christopher Larson, Media, PA (US); Madeline Repollet, Fort Washington, PA (US); Herman Rutner, Hatboro, PA (US); Leon W. M. M. Terstappen, Huntingdon Valley, PA (US); Shawn Mark O'Hara, Ambler, PA (US); Steven Gross, Ambler, PA (US)

(73) Assignee: Veridex, LLC, Raritan, NJ (US)

( * ) Notice: Subject to any disclaimer, the term of this patent is extended or adjusted under 35 U.S.C. 154(b) by 472 days.

(21) Appl. No.: 10/780,399

(22) Filed: Feb. 17, 2004

(65) Prior Publication Data

US 2005/0181463 A1 Aug. 18, 2005

(51) Int. Cl.
- *A01N 1/02* (2006.01)
- *G01N 33/574* (2006.01)
- *G01N 33/553* (2006.01)
- *G01N 33/00* (2006.01)

(52) U.S. Cl. .......................... 435/7.23; 435/2; 435/7.21; 435/7.24; 435/7.94; 435/287.2; 436/501; 436/526; 436/538; 436/10; 436/175; 436/177; 436/813; 422/61; 422/73; 422/101; 533/388.8; 533/389.7; 533/413

(58) Field of Classification Search ..................... 435/2, 435/7.21, 7.23, 7.24, 287.2, 962, 7.94; 436/526, 436/518, 64, 164, 175, 177, 813, 824, 825, 436/501, 538, 10; 530/388.8, 389.7, 413; 422/61, 73, 101
See application file for complete search history.

(56) References Cited

U.S. PATENT DOCUMENTS 3,970,518 A 7/1976 Giaever (Continued)

FOREIGN PATENT DOCUMENTS

WO 00/47998 A1 8/2000

(Continued)

OTHER PUBLICATIONS

Carbonari et al., Detection and Characterization of Apoptotic Peripheral Blood Lymphocytes in Human Immunodeficiency Virus Infection and Cancer Chemotherapy by a Novel Flow Immunocytometric Method, Blood 83 (5): 1266-1277 (Mar. 1, 1994).*

(Continued)

*Primary Examiner*—Gailene R Gabel

(57) ABSTRACT

The methods and reagents described in this invention are used to analyze circulating tumor cells, clusters, fragments, and debris. Analysis is performed with a number of platforms, including flow cytometry and the CellSpotter® fluorescent microscopy imaging system. Analyzing damaged cells has shown to be important. However, there are two sources of damage: in vivo and in vitro. Damage in vivo occurs by apoptosis, necrosis, or immune response. Damage in vitro occurs during sample acquisition, handling, transport, processing, or analysis. It is therefore desirable to confine, reduce, eliminate, or at least qualify in vitro damage to prevent it from interfering in analysis. Described herein are methods to diagnose, monitor, and screen disease based on circulating rare cells, including malignancy as determined by CTC, clusters, fragments, and debris. Also provided are kits for assaying biological specimens using these methods.

16 Claims, 6 Drawing Sheets

U.S. PATENT DOCUMENTS

| | | | |
|---|---|---|---|
| 4,018,886 A | 4/1977 | Giaever | |
| 4,040,785 A | 8/1977 | Kim et al. | |
| 4,230,685 A | 10/1980 | Senyei et al. | |
| 4,267,234 A | 5/1981 | Rembaum | |
| 4,320,111 A | 3/1982 | Hirsch et al. | |
| 4,452,773 A | 6/1984 | Molday | |
| 4,554,088 A | 11/1985 | Whitehead et al. | |
| 4,647,283 A | 3/1987 | Carpentier et al. | |
| 4,659,678 A | 4/1987 | Forrest | |
| 4,788,139 A | 11/1988 | Ryan | |
| 4,795,698 A | 1/1989 | Owens et al. | |
| 5,200,084 A * | 4/1993 | Liberti et al. | 210/695 |
| 5,385,707 A | 1/1995 | Miltenyi et al. | |
| 5,597,531 A | 1/1997 | Liberti et al. | |
| 5,698,271 A | 12/1997 | Liberti et al. | |
| 5,849,517 A | 12/1998 | Ryan | |
| 5,876,593 A | 3/1999 | Liberti et al. | |
| 5,985,153 A | 11/1999 | Dolan et al. | |
| 6,136,182 A | 10/2000 | Dolan | |
| 6,190,870 B1 * | 2/2001 | Schmitz et al. | 435/7.23 |
| 6,197,523 B1 | 3/2001 | Rimm | |
| 6,265,229 B1 * | 7/2001 | Fodstad et al. | 436/526 |
| 6,861,259 B2 | 2/2002 | Columbus | |
| 6,365,362 B1 * | 4/2002 | Terstappen et al. | 435/7.23 |
| 2001/0024802 A1 | 9/2001 | Rimm et al. | |
| 2002/0164825 A1 | 11/2002 | Chen | |
| 2004/0072269 A1 | 4/2004 | Rao et al. | |

FOREIGN PATENT DOCUMENTS

| | | |
|---|---|---|
| WO | 02/20825 A1 | 3/2002 |
| WO | 03/018757 A2 | 3/2003 |

OTHER PUBLICATIONS

Butler, T. et al., 1975 Cancer Research, 35:512-516.

Moreno, J.G. et al., "Changes in Circulating Carcinoa Cells in Patients with Metastic Prostate Cancer Correlates with Disease State," Urology 58, 2001.

Brandt, B. et al., "Isolation of prostate-derived single cells and cell clusters from human peripheral blood," Cancer Research 56, p. 4556-4561, 1996.

American Association for Cancer Research, 93rd Annual Meeting, Apr. 6-10, 2002, San Francisco, CA, USA, vol. 43, Mar. 2002.

Kagan, M. et al., "A Sample Preparation and Analysis System for Identification of Circulating Tumor Cells," Journal of Clinical Ligand Assay, vol. 25, No. 1, Spring 2002.

Liberti, P.A. et al., "Bioreceptor Ferrofluids: Novel Characteristics and Their Utility in Medical Applications," E. Pelizzeni (ed.), Fine Particles Science and Technology, pp. 777-790, 1996.

Tanaka et al., "Immunohistochemical study of localization of extracellular matrix after helium YAG laser irrigationin rat cornea," Japanese Journal of Ophthalmology, Sep.-Oct. 2000, vol. 44, No. 5, pp. 482-484.

Martin et al., "From genomics to proteomics: techniques and applications in cancer research," Trends in Cell Biology, Nov. 2001, vol. 11, No. 11, pp. S60-S65.

Zheng-Pin et al., "Identification and Characterization of Circulating Prostate Carcinoma Cells," Cancer, Jun. 15, 2000, vol. 88, No. 12, pp. 2787-2795.

* cited by examiner

ANALYSIS OF CIRCULATING TUMOR CELLS, FRAGMENTS, AND DEBRIS

PRIORITY INFORMATION

This application claims priority under 35 USC §119(e) to U.S. Provisional Applications No. 60/314,151 filed 23 Aug. 2001, and No. 60/369,628 filed 3 Apr. 2002. Both of these applications are incorporated by reference herein.

BACKGROUND OF THE INVENTION

Many clinicians believe that cancer is an organ-confined disease in its early stages. However, it appears that this notion is incorrect, and cancer is often a systemic disease by the time it is first detected using methods currently available. There is evidence that primary cancers begin shedding neoplastic cells into the circulation at an early disease stage prior to the appearance of clinical manifestations. Upon vascularization of a tumor, tumor cells shed into the circulation may attach and colonize at distant sites to form metastases. These circulating tumor cells (CTC) contain markers not normally found in healthy individuals' cells, thus forming the basis for diagnosis and treatment of specific carcinomas. Hence, the presence of tumor cells in the circulation can be used to screen for cancer in place of, or in conjunction with, other tests, such as mammography, or measurements of PSA. By employing appropriate monoclonal antibodies directed to associated markers on or in target cells, or by using other assays for cell protein expression, or by the analysis of cellular mRNA, the organ origin of such cells may readily be determined, e.g., breast, prostate, colon, lung, ovarian or other non-hematopoietic cancers.

Thus, in cases where cancer cells can be detected, while there are essentially no clinical signs of a tumor, it will be possible to identify their presence as well as the organ of origin. Furthermore, based on clinical data, cancer should be thought of as a blood borne disease characterized by the presence of potentially very harmful metastatic cells, and therefore, treated accordingly. In cases where there is absolutely no detectable evidence of CTC, e.g., following surgery, it may be possible to determine from further clinical study whether follow-up treatment, such as radiation, hormone therapy or chemotherapy is required. Predicting the patient's need for such treatment, or the efficacy thereof, given the costs of such therapies, is a significant and beneficial piece of clinical information. It is also clear that the number of tumor cells in the circulation is related to the stage of progression of the disease, from its inception to the final phases of disease.

Malignant tumors are characterized by their ability to invade adjacent tissue. In general, tumors with a diameter of 1 mm are vascularized and animal studies show that as much as 4% of the cells present in the tumor can be shed into the circulation in a 24 hour period (Butler, TP & Gullino PM, 1975 *Cancer Research* 35:512-516). The shedding capacity of a tumor is most likely dependent on the aggressiveness of the tumor. Although tumor cells are shed into the circulation on a continuous basis, it is believed that none or only a small fraction will give rise to distant metastasis (Butler & Gullino, supra). Increase in tumor mass might be expected to be proportional to an increase in the frequency of the circulating tumor cells. If this were found to be the case, methods available with a high level of sensitivity would facilitate assessment of tumor load in patients with distant metastasis as well as those with localized disease. Detection of tumor cells in peripheral blood of patients with localized disease has the potential not only to detect a tumor at an earlier stage but also to provide indications as to the potential invasiveness of the tumor.

However, whole blood is a complex body fluid containing diverse populations of cellular and soluble components capable of undergoing numerous biochemical and enzymatic reactions in vivo and in vitro, particularly on prolonged storage for more than 24 hrs. Some of these reactions are related to immunoreactive destruction of circulating tumor cells that are recognized as foreign species. The patient's immune response weakens or destroys tumor cells by the normal defense mechanisms including phagocytosis and neutrophil activation. Chemotherapy similarly is intended to reduce both cell function and proliferation by inducing cell death by necrosis. Besides these external destructive factors, tumor cells damaged in a hostile environment may undergo programmed death or apoptosis. Normal and abnormal cells (including CTC) undergoing apoptosis or necrosis, have altered membrane permeabilities that allow escape of DNA, RNA, and other intracellular components leading to formation of damaged cells, fragmented cells, cellular debris, and eventual complete disintegration. Such tumor cell debris may still bear epitopes or determinants characteristic of intact cells and can lead to spurious increases in the number of detected circulating cancer cells. Whole blood specimens from healthy individuals also have been observed to undergo destruction of labile blood cell components, herein categorized as decreased blood quality, on prolonged storage for periods of greater than 24 hours. For example, erythrocytes may rupture and release hemoglobin and produce cell ghosts. Leukocytes, particularly granulocytes, are known to be labile and diminish on storage. Such changes increase the amount of cellular debris that can interfere with the isolation and detection of rare target cells such as CTC. The combined effects of these destructive processes can substantially increase cellular debris, which is readily detectable, for instance, in flow cytometric and microscopic analyses, such as CELLSPOTTER, an image analysis device, or CELLTRACKS®, a semi-automated image analysis device, which are described in commonly-owned U.S. Pat. Nos. 5,985,153 and 6,136,182, both of which are incorporated by reference herein.

Detection of circulating tumor cells by microscopic imaging is similarly adversely affected by spurious decreases in classifiable tumor cells and a corresponding increase in interfering stainable debris. Hence, maintaining the integrity or the quality of the blood specimen is of utmost importance, since there may be a delay of as much as 24 hours between blood draw and specimen processing. Such delays are to be expected, since the techniques and equipment used in processing blood for this assay may not be readily available in every laboratory. The time necessary for a sample to arrive at a laboratory for sample processing may vary considerably. It is therefore important to establish the time window within which a sample can be processed. In routine hematology analyses, blood samples can be analyzed within 24 hours. However, as the analysis of rare blood cells is more critical, the time window in which a blood sample can be analyzed is shorter. An example is immunophenotyping of blood cells, which, in general, must be performed within 24 hours. In a cancer cell assay, larger volumes of blood have to be processed, and degradation of the blood sample can become more problematic as materials released by disintegrating cells, both from CTC and from hematopoietic cells, can increase the background and therefore decrease the ability to detect tumor cells.

The origin and nature of observed small debris and large clump-like aggregates are not fully understood, but are believed to involve cellular components or elements originating from target cells, non-target cells, and possibly plasma components. Since CTC can be considered immunologically foreign species, normal cellular immune responses of the host will occur in vivo even before blood draw. Also large numbers of CTC can be continuously shed from a tumor site, and a steady-state level is maintained in which destruction of CTC equals the shedding rate which in turn depends on the size of the tumor burden (see J G Moreno et al. "Changes in Circulating Carcinoma Cells in Patients with Metastatic Prostate Cancer Correlates with Disease State." *Urology* 58. 2001).

Various methods are known in this particular art field for recovering tumor cells from blood. For example, U.S. Pat. No. 6,190,870 to AmCell and Miltenyi teaches immunomagnetic isolation followed by flow cytometric enumeration. However, before immunomagnetic separation, the blood samples are pre-processed using density gradients. Furthermore, there is no discussion of isolating or counting anything other than intact cells. There is also no visual analysis of the samples.

In U.S. Pat. No. 6,197,523, Rimm et al. describe enumerating cancer cells in 100 µl blood samples. The methods use capillary microscopy to confirm the identity of cells that are found. The methods are specific for intact cells, and there is no discussion of isolating or enumerating anything else, such as fragments or debris.

In U.S. Pat. No. 6,365,362 to Immunivest, methods are described for immunomagnetically enriching and analyzing samples for tumor cells in blood. The methods are specifically directed towards analyzing intact cells, where the number of cells correlates with the disease state. The isolated cells are labeled for the presence of nucleic acid and an additional marker, which allows the exclusion of non-target sample components during analysis.

In WO02/20825, Chen describes using an adhesion matrix for enumerating tumor cells. Briefly, the matrix is coated with specific adhesion molecules that will bind to cancer cells with metastatic potential. The matrix can then be analyzed for the presence and type of captured cells. Also described are methods for using the matrix in screening treatments. While steps are taken to discriminate between intact cells and apoptotic or necrotic cells, the apoptotic or necrotic cells are specifically excluded from analysis.

In WO00/47998, two pathways are described for CTC, terminal and proliferative. Both pathways begin with an "indeterminate" cell that progresses, as determined by morphological differences, down either the terminal or proliferative pathway. A cell in the terminal pathway eventually is destroyed, and a cell in the proliferative pathway will form a new metastatic colony as a metastatic tumor. These two pathways were designed to explain morphological differences seen in patient samples.

Generally, the more resistant and proliferative cells survive to establish secondary or metastatic sites. In the peripheral circulation, CTC are further attacked in vivo (and also in vitro) by activated neutrophils and macrophages resulting progressively in membrane perforation, leakage of electrolytes, smaller molecules, and eventual loss of critical cellular elements including DNA, chromatin, etc, which are essential for cell viability. At a critical point of the cell's demise, cell destruction is further assisted by apoptosis. Apoptosis is characterized by a series of stepwise slow intracellular events, which differs from necrosis or rapid cell death triggered or mediated by an extracellular species, e.g. a cytotoxic anti-tumor drug. All or some of these destructive processes may lead to formation of debris and/or aggregates including stainable DNA, DNA fragments and "DNA ladder" structures from disintegrating CTC as well as from inadvertent destruction of normal hematopoietic cells during drug therapy, since most cytotoxic drugs are administered at near toxic doses.

As shown in WO00/47998, U.S. Pat. No. 6,190,870 and other publications, CTC can circulate as both live and dead cells, wherein "dead" comprises the full range of damaged and fragmented cells as well as CTC-derived debris. The tumor burden is probably best represented by the total of both intact CTC and of damaged CTC, which bear morphological characteristics of cells. However, some damaged cells, may have large pores allowing leakage of the liquid and particulate cytosolic contents resulting in a change in the buoyant densities from about 1.06-1.08 to greater than 1.12, or well above the densities of RBC (live and dead cells can be separated at the interface of gradients of d=1.12 and 1.16 according to a Pharmacia protocol). Conventional density gradients, as used in WO00/47998 would lose such damaged CTC in the discarded RBC layer having a range in density of about 1.08 to 1.11. CTC debris that is positively stained for cytokeratin may also have densities falling in the RBC or higher ranges, since most intracellular components (with the possible exception of lipophilic membrane fragments) have densities in the range of 1.15 to 1.3. Hence, a substantial portion of damaged CTC and CTC debris may be located in or below the RBC layer, and would not be seen by the density gradient methods in WO00/47998. Some images of damaged or fragmented CTC are shown, but it is quite possible the damage occurred during cytospin or subsequent processing, and is thus artifactual. While the densities of most intact tumor cells may fall in the WBC region, it is quite likely that damaged CTC in patient samples have higher densities that may place them in the RBC layer; outside the reach of gradient techniques.

U.S. patent application No. 2001/0024802 describes methods for binding fragments and debris to beads. That published application described numerous possibilities for the density of fragments and debris of interest. Upon centrifugation, the beads will be located in a layer above RBC, because of the pre-determined specific gravity (density) of the beads coupled to fragments and/or debris. However, this system is dependent on correctly binding fragments and debris to these beads. If any other sample component binds the beads, they may not appear in the desired location, and subsequently will not be subject to analysis.

Epithelial cells in their tissue of origin obey established growth and development "rules". Those rules include population control. This means that under normal circumstances the number and size of the cells remains constant and changes only when necessary for normal growth and development of the organism. Only the basal cells of the epithelium or immortal cells will divide and they will do so when it is necessary for the epithelium to perform its function, whatever it is depending in the nature and location of the epithelium. Under some abnormal but benign circumstances, cells will proliferate and the basal layer will divide more than usual, causing hyperplasia. Under some other abnormal but benign circumstances, cells may increase in size beyond what is normal for the particular tissue, causing cell gigantism, as in folic acid deficiency.

Epithelial tissue may increase in size or number of cells also due to pre-malignant or malignant lesions. In these cases, changes similar to those described above are accompanied by nuclear abnormalities ranging from mild in low-grade intraepithelial lesions to severe in malignancies. It is believed that changes in these cells may affect portions of the thickness of the epithelium and as they increase in severity will comprise a thicker portion of such epithelium. These cells do not obey restrictions of contact inhibition and continue growing without tissue controls. When the entire thickness of the epithelium is affected by malignant changes, the condition is recognized as a carcinoma in situ (CIS).

The malignant cells eventually are able to pass through the basement membrane and invade the stroma of the organ as their malignant potential increases. After invading the stroma, these cells are believed to have the potential for reaching the blood vessels. Once they infiltrate the blood vessels, the malignant cells find themselves in a completely different environment from the one they originated from.

The cells may infiltrate the blood vessels as single cells or as clumps of two or more cells. A single cell of epithelial origin circulating through the circulatory system is destined to have one of two outcomes. It may die or it may survive.

Single Cells:

The cell may die either through apoptosis due to internal changes or messages in the cell itself. These messages may have been in the cell before intravasation or they may be received while in the blood, or it may die due to the influence of the immune system of the host, which may recognize these cells as "alien" to this environment. The results of cellular death are identifiable in CELLSPOTTER, an image analysis device. as enucleated cells, speckled cells or amorphous cells. These cells do not have the potential for cell division or for establishing colonies or metastases.

Enucleated cells are the result of nuclear disintegration and elimination-karyorrhexis and karyolysis. They are positive for cytokeratin, and negative for nucleic acid.

The speckled cells are positive for cytokeratin and DAPI and show evidence of cellular degeneration and cytoplasmic disintegration. These cells may represent response to therapy or to the host's immune system as the cytoskeletal proteins retract.

Another dying tumor cell identifiable using CELLSPOTTER, an image analysis device, is the amorphous cell. These cells are probably damaged during the preparation process, a sign that these may be weaker, more delicate cells but may also be the result of apoptosis or immune attack.

A single epithelial malignant cell may have the potential to survive the circulation and form colonies in distant organs. These "survivor cells" appear in CELLSPOTTER, an image analysis device, as intact cells with high nuclear material/ cytoplasmic material ratio. These cells are probably undifferentiated and can potentially divide in blood and form small clumps that may extravasate in a distant capillary, where the cell may establish a new colony, or it may remain as a single cell until it extravasates, dividing once it establishes itself in the new tissue, starting this way a new colony.

Clusters: The primary tumor may shed clusters that enter the circulation as described by B Brandt et al. ("Isolation of prostate-derived single cells and cell clusters from human peripheral blood." *Cancer Research* 56 p4556-4561, 1996). These clusters may remain as clusters and invade a distant tissue or they may become dissociated in the circulation, probably due to differences in pressure in blood or to the immune system's intervention. If these cells are dissociated into single cells, they may follow one of the two paths described for single cells above (see 1 and 2). Cluster formations may have an effect in survival by using the outside cells as a shield that protects the inner cells from the immune system.

Once a new colony is established in a new organ, some malignant cells will continue replicating to form a new tumor. If they reach new capillaries, the metastasis story may be repeated and a secondary metastasis occurs.

Monitoring of treatment in patients with known carcinomas: A decrease in the number of tumor cells and/or increase in the response index may represent a response to patient therapy.

Total tumor cells=Dying cells+Survivor cells (TTC=DC+ SC)

Response Index=dying cells/total tumor cells (RI=DC/ TTC).

The higher the response index, the better the response to therapy. A low response index may indicate that the patient is not responding to the treatment and or that the pt's immune system is not able to handle the tumor load.

A patient who has 50 total tumor cells that were all survivor cells at pre-treatment visit (a RI=0/50=0) and has 50 TTC on follow-up (after treatment) visit may have different outcomes depending in the RI. If all the TTC are SC (i.e. DC=0), there was no response to therapy. If there are 50 cells but the response index is 40/50=0.8, then either the immune system or the therapy is having a negative effect on tumor load, therefore, is a positive response.

Decisions in follow-up on patients with known pre-malignancies: When a pap smear is diagnosed as having cells with atypical or low-grade intraepithelial lesions, there is always the possibility that these patients have a more severe abnormality, which cells were missed as a sampling error. These patients can be colposcoped and biopsied or they may be asked to return in three months for a repeat pap smear. If the atypical cells were concurrent with a small focal area of malignant cells that did not get sampled, the patient will wait 3 months before she gets any follow-up. This may explain why some pre-malignancies seem to progress quicker than others (misdiagnoses due to sampling error, causing an artifact in statistics). These are usually explained as being a more "aggressive" pre-malignancy. CELLSPOTTER, an image analysis device, can be used to help in the decision tree of these patients. All patients with an abnormal pap (5-10% of the pap smears in the USA) can immediately be tested for circulating epithelial cells. Patients with positive tests should be followed-up immediately and aggressively. Patients with negative results may wait the three months for the repeat pap. This would simplify the decision making process for the physician and health professionals and help the patient trust her follow-up procedure.

Screening: CELLSPOTTER, an image analysis device, image analysis may be used for screening of the general population with the condition that special, tissue specific antibodies would be used on a second test on all abnormal samples. Identification of CTC in a patient may indicate that there is a primary malignancy that has started or is starting the process of metastasis. If these cells are identified as of the tissue of origin with new markers, then organ specific tests, like CT guided fine needle aspirations (FNA) can be used to verify the presence or absence of such malignancies. Patients where a primary cannot be identified may be followed-up with repeat tests after establishing an individual base line.

In summary, all or some of the above-cited factors can and were found to contribute to debris and/or aggregate formation that have been observed to confound the detection of CTC by direct enrichment procedures from whole blood as disclosed in this invention. The number of intact CTC, damaged or suspect CTC as well as the degree of damage to the CTC, may further serve as diagnostically important indicators of the tumor burden, the proliferative potential of the tumor cells and/or the effectiveness of therapy. In contrast, the methods and protocols of the prior art combine unavoidable in vivo damage to CTC with avoidable in vitro storage and processing damage, thus yielding erroneous information on CTC and tumor burdens in cancer patients. Finally, the relatively simple blood test of the present invention described herein, which functions with a high degree of sensitivity and specificity, the test can be thought of as a "whole body biopsy."

BRIEF DESCRIPTION OF THE INVENTION

The methods and reagents described in this invention are used to analyze circulating tumor cells, fragments, and debris. Analysis is performed with a number of platforms, including multiparameter flow cytometry and the CELLSPOTTER fluorescent microscopy imaging system. It is possible to mimic the damaged CTC that forms fragments and debris. Furthermore, the number of fragments and debris can be correlated back to the number of circulating tumor cells (CTC). It is also possible to inhibit further damage of CTC between the blood draw and sample processing through the use of stabilizing agents.

It has been shown herein that the ability to differentiate between in vitro damage, caused by specimen acquisition, transport, storage, processing, or analysis, and in vivo damage, caused by apoptosis, necrosis, or the patient's immune system. Indeed, it is desirable to confine, reduce, eliminate, or at least qualify in vitro damage to prevent it from interfering in analysis.

Herein are described methods to diagnose, monitor, and screen disease based on circulating rare cells, including malignancy as determined by CTC, clusters, fragments, and debris. Also provided are kits for assaying biological specimens using these methods.

DETAILED DESCRIPTION OF THE INVENTION

Figure 1A:
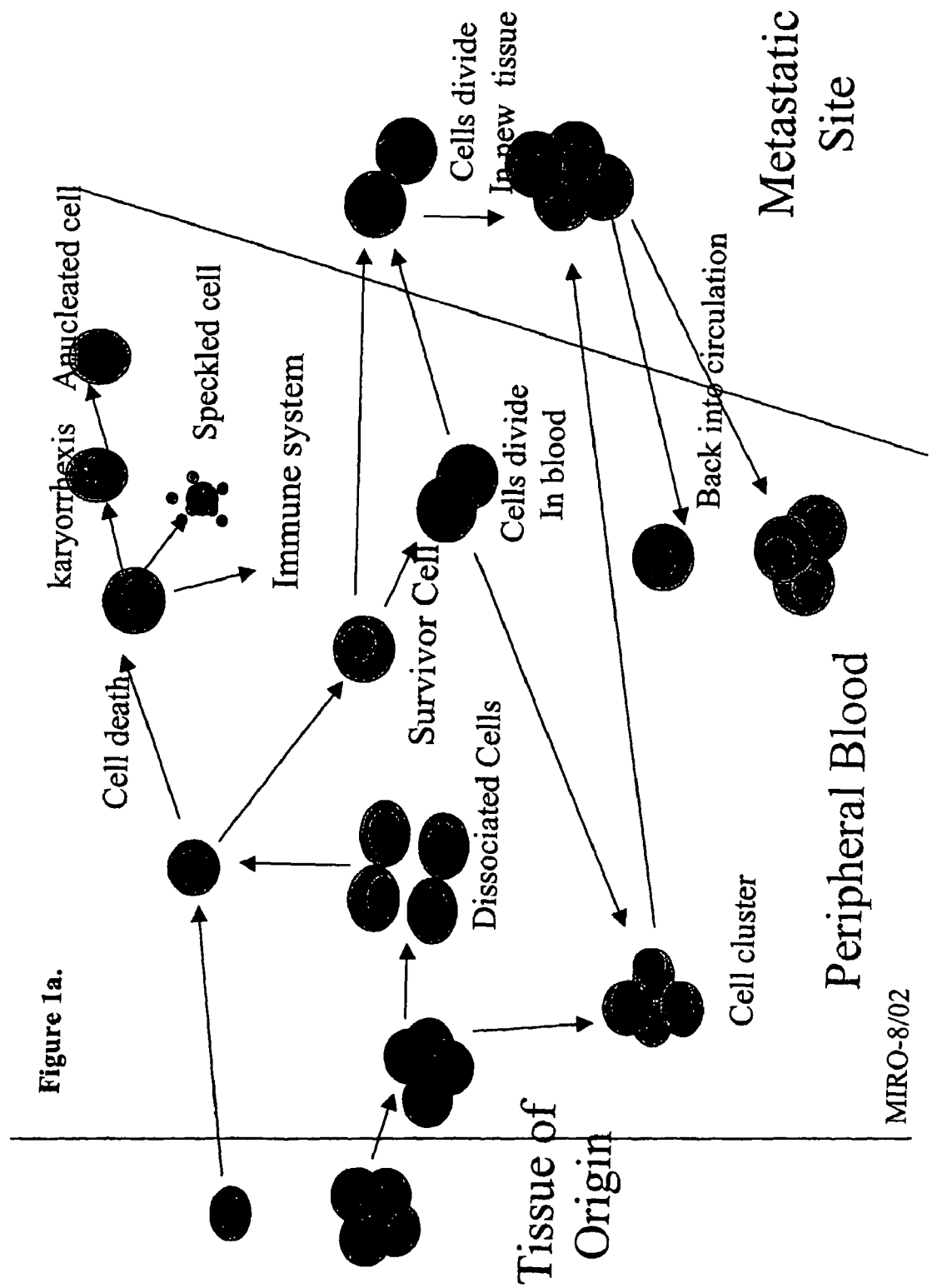
FIG. 1—Models of tumor shedding and metastasis. 1a. shows possible stages of cells, clusters, and fragments. 1b. shows the same model with actual images from samples.

Herein, various terms that are well understood by those of ordinary skill in the art are used. The intended meaning of these terms does not depart from the accepted meaning.

The evidence that minimal residual disease in patients with carcinoma has clinical significance is mounting. To effectively monitor minimal residual disease, a qualitative and quantitative assessment is needed. As the frequency of carcinoma cells in blood or bone marrow is low the laborious manual sample preparation methods involved in the preparation of samples for analysis often leads to erroneous results. To overcome these limitations a semi-automated sample preparation system was developed that minimize variability and provide more consistent results, as described in commonly-owned pending U.S. application Ser. No. 10/081,996, filed 20 Feb. 2002, which is incorporated by reference herein.

Various methods are available for analyzing or separating the above-mentioned target substances based upon complex formation between the substance of interest and another substance to which the target substance specifically binds. Separation of complexes from unbound material may be accomplished gravitationally, e.g. by settling, or, by centrifugation of finely divided particles or beads coupled to the target substance. Such particles or beads may be made magnetic to facilitate the bound/free separation step. Magnetic particles are well known in the art, as is their use in immune and other bio-specific affinity reactions. Generally, any material that facilitates magnetic or gravitational separation may be employed for this purpose. However, it has become clear that magnetic separation means are the method of choice.

Magnetic particles can be classified on the basis of size; large (1.5 to about 50 microns), small (0.7-1.5 microns), or colloidal (<200 nm), which are also referred to as nanoparticles. The third, which are also known as ferrofluids or ferrofluid-like materials and have many of the properties of classical ferrofluids, are sometimes referred to herein as colloidal, superparamagnetic particles.

Small magnetic particles of the type described above are quite useful in analyses involving bio-specific affinity reactions, as they are conveniently coated with biofunctional polymers (e.g., proteins), provide very high surface areas and give reasonable reaction kinetics. Magnetic particles ranging from 0.7-1.5 microns have been described in the patent literature, including, by way of example, U.S. Pat. Nos. 3,970,518; 4,018,886; 4,230,685; 4,267,234; 4,452,773; 4,554,088; and 4,659,678. Certain of these particles are disclosed to be useful solid supports for immunological reagents.

The efficiency with which magnetic separations can be done and the recovery and purity of magnetically labeled cells will depend on many factors. These include:
number of cells being separated,
receptor or epitope density of such cells,
magnetic load per cell,
non-specific binding (NSB) of the magnetic material,
carry-over of entrapped non-target cells,
technique employed,
nature of the vessel,
nature of the vessel surface,
viscosity of the medium, and
magnetic separation device employed.

If the level of non-specific binding of a system is substantially constant, as is usually the case, then as the target population decreases so will the purity.

As an example, a system with 0.8% NSB that recovers 80% of a population which is at 0.25% in the original mixture will have a purity of 25%. Whereas, if the initial population was at 0.01% (one target cell in $10^6$ bystander cells), and the NSB were 0.001%, then the purity would be 8%. Hence, a high the purity of the target material in the specimen mixture results in a more specific and effective collection of the target material. Extremely low non-specific binding is required or advantageous to facilitate detection and analysis of rare cells, such as epithelial derived tumor cells present in the circulation.

Less obvious is the fact that the smaller the population of a targeted cell, the more difficult it will be to magnetically label and to recover. Furthermore, labeling and recovery will markedly depend on the nature of magnetic particle employed. For example, when cells are incubated with large magnetic particles, such as Dynal beads, cells are labeled through collisions created by mixing of the system, as the beads are too large to diffuse effectively. Thus, if a cell were present in a population at a frequency of 1 cell per ml of blood or even less, as may be the case for tumor cells in very early cancers, then the probability of labeling target cells will be related to the number of magnetic particles added to the system and the length of time of mixing. Since mixing of cells with such particles for substantial periods of time would be deleterious, it becomes necessary to increase particle concentration as much a possible. There is, however, a limit to the quantity of magnetic particle that can be added, as one can substitute a rare cell mixed in with other blood cells for a rare cell mixed in with large quantities of magnetic particles upon separation. The latter condition does not markedly improve the ability to enumerate the cells of interest or to examine them.

The preferred magnetic particles for use in carrying out this invention are particles that behave as colloids. Such particles are characterized by their sub-micron particle size, which is generally less than about 200 nm (0.20 microns), and their stability to gravitational separation from solution for extended periods of time. In addition to the many other advantages, this size range makes them essentially invisible to analytical techniques commonly applied to cell analysis. Particles within the range of 90-150 nm and having between 70-90% magnetic mass are contemplated for use in the present invention. Suitable magnetic particles are composed of a crystalline core of superparamagnetic material surrounded by molecules which are bonded, e.g., physically absorbed or covalently attached, to the magnetic core and which confer stabilizing colloidal properties. The coating material should preferably be applied in an amount effective to prevent non-specific interactions between biological macromolecules found in the sample and the magnetic cores. Such biological macromolecules may include carbohydrates such as sialic acid residues on the surface of non-target cells, lectins, glycoproteins, and other membrane components. In addition, the material should contain as much magnetic mass per nanoparticle as possible. The size of the magnetic crystals comprising the core is sufficiently small that they do not contain a complete magnetic domain. The size of the nanoparticles is sufficiently small such that their Brownian energy exceeds their magnetic moment. As a consequence, North Pole, South Pole alignment and subsequent mutual attraction/repulsion of these colloidal magnetic particles does not appear to occur even in moderately strong magnetic fields, contributing to their solution stability. Finally, the magnetic particles should be separable in high magnetic gradient external field separators. That characteristic facilitates sample handling and provides economic advantages over the more complicated internal gradient columns loaded with ferromagnetic beads or steel wool. Magnetic particles having the above-described properties can be prepared by modification of base materials described in U.S. Pat. Nos. 4,795,698, 5,597,531, and 5,698,271, each incorporated by reference herein.

An improved method for making particles is described in U.S. Pat. No. 5,698,271. These materials are an improvement over those disclosed in the '531 patent in that the process includes a high temperature coating step which markedly increases the level of coating. Nanoparticles made with bovine serum albumin (BSA) coating using this process, for example, have a 3-5-fold lower non-specific binding characteristic for cells when compared to the DC-BSA materials of '531. This decrease in non-specific binding has been shown to be directly due to the increased level of BSA coating material. When such nanoparticles were treated so as to remove BSA coating, non-specific binding returns to high levels. It was thus determined that a direct relationship exists between the amount of BSA coated on iron oxide crystal surfaces and the nonspecific binding of cells. Typically, the non-specific binding of cells from whole blood with these particles was 0.3%, which is significantly better than those, produced from '531. Thus, from 10 ml of whole blood there would be about 200,000 non-target cells that would also be isolated with the cells targeted for enrichment.

Since small nanoparticles (30-70 nm) will diffuse more readily they will preferentially label cells compared with their larger counterparts. When very high gradients are used, such as in internal gradient columns, the performance of these materials, regardless of size, makes little difference. On the other hand, when using external gradients, or gradients of lesser magnitude than can be generated on microbead or steel wool columns, the occupancy of small nanoparticles on cells has a significant effect. This was conclusively shown to be the case by fractionating DC nanoparticles and studying the effects on recovery. Based on these studies and other optimization experiments, means for fractionating nanoparticles magnetically or on columns was established where base coated magnetic particles could be prepared that were devoid of excessively small or large nanoparticles. For example, base coated particles of mean diameter 100 nm can be produced which contain at best trace amounts of material smaller than 80 nm or over 130 nm. Similarly material of about 120 nm can be made with no appreciable material smaller than 90-95 nm and over 160 nm. Such materials performed optimally with regard to recovery and could be made sub-optimal by the inclusion of 60-70 nm nanoparticles. The preferred particle size range for use in practicing this invention is 90-150 nm for base coated magnetic particles, e.g., BSA-coated magnetite.

Based on the foregoing, high gradient magnetic separation with an external field device employing highly magnetic, low non-specific binding, colloidal magnetic particles is the method of choice for separating a cell subset of interest from a mixed population of eukaryotic cells, particularly if the subset of interest comprises but a small fraction of the entire population. Such materials, because of their diffusive properties, readily find and magnetically label rare events, such as tumor cells in blood. For magnetic separations for tumor cell analysis to be successful, the magnetic particles must be specific for epitopes that are not present on hematopoeitic cells.

A large variety of analytical methods and criteria are used to identify tumor cells, and the first attempts are being undertaken to standardize criteria that define what constitutes a tumor cell by immunocytochemistry. In this study, blood samples from prostate cancer patients were immunomagnetically enriched for cells that expressed EpCAM. Tumor cells were identified by the expression of the cytoskeletal proteins cytokeratin (CK+), the absence of the common leukocyte antigen CD45 (CD45−) and the presence of nucleic acids (NA+) by multicolor fluorescence analysis. Rare events or rare cells can be immunophenotyped by both flowcytometry and fluorescence microscopy. Flowcytometric analysis excels in its ability to reproducibly quantify even low levels of fluorescence whereas microscopy has the better specificity as morphological features can aid in the classification of the immunophenotypically identified objects. Although there was a correlation between the number of CTC detected in blood of prostate cancer patients by flowcytometry and microscopy, microscopic examination of the CK+, CD45−, NA+ objects showed that only few of the objects appeared as intact cells. This observation agrees with other reports that showed apoptosis in a substantial portion of circulating tumor cells.

The terms "biological specimen" or "biological sample" may be used interchangeably, and refer to a small potion of fluid or tissue taken from a human subject that is suspected to contain cells of interest, and is to be analyzed. A biological specimen refers to the fluidic portion, the cellular portion, and the portion containing soluble material. Biological specimens or biological samples include, without limit bodily fluids, such as peripheral blood, tissue homogenates, nipple aspirates, colonic lavage, sputum, bronchial lavage, and any other source of cells that is obtainable from a human subject. An exemplary tissue homogenate may be obtained from the sentinel node in a breast cancer patient.

The term "rare cells" is defined herein as cells that are not normally present in biological specimens, but may be present as an indicator of an abnormal condition, such as infectious disease, chronic disease, injury, or pregnancy. Rare cells also refer to cells that may be normally present in biological specimens, but are present with a frequency several orders of magnitude less than cells typically present in a normal biological specimen.

The term "determinant", when used in reference to any of the foregoing target bioentities, refers broadly to chemical mosaics present on macromolecular antigens that often induce an immune response. Determinants may also be used interchangeably with "epitopes". A "biospecific ligand" or a "biospecific reagent," used interchangeably herein, may specifically bind determinants. A determinant refers to that portion of the target bioentity involved in, and responsible for, selective binding to a specific binding substance (such as a ligand or reagent), the presence of which is required for selective binding to occur. In fundamental terms, determinants are molecular contact regions on target bioentities that are recognized by agents, ligands and/or reagents having binding affinity therefore, in specific binding pair reactions.

The term "specific binding pair" as used herein includes antigen-antibody, receptor-hormone, receptor-ligand, agonist-antagonist, lectin-carbohydrate, nucleic acid (RNA or DNA) hybridizing sequences, Fc receptor or mouse IgG-protein A, avidin-biotin, streptavidin-biotin and virus-receptor interactions.

The term "detectably label" is used herein to refer to any substance whose detection or measurement, either directly or indirectly, by physical or chemical means, is indicative of the presence of the target bioentity in the test sample. Representative examples of useful detectable labels, include, but are not limited to the following: molecules or ions detectable based on light absorbance, fluorescence, reflectance, light scatter, phosphorescence, or luminescence properties; molecules or ions detectable by their radioactive properties; molecules or ions detectable by their nuclear magnetic resonance or paramagnetic properties. Included among the group of molecules indirectly detectable based on light absorbance or fluorescence, for example, are various enzymes which cause appropriate substrates to convert (e.g. from non-light absorbing to light absorbing molecules, or form non-fluorescent to fluorescent molecules). Analysis can be performed using any of a number of commonly used platforms, including multi-parameter flow cytometry immunofluorescent microscopy, laser scanning cytometry, bright field base image analysis, capillary volumetry, spectral imaging analysis, manual cell analysis, CELLSPOTTER analysis, CELLTRACKS™ analysis, and automated cell analysis.

The phrase "to the substantial exclusion of" refers to the specificity of the binding reaction between the biospecific ligand or biospecific reagent and its corresponding target determinant. Biospecific ligands and reagents have specific binding activity for their target determinant yet may also exhibit a low level of non-specific binding to other sample components.

The phrase "early stage cancer" is used interchangeably herein with "Stage I" or "Stage II" cancer and refers to those cancers that have been clinically determined to be organ-confined. Also included are tumors too small to be detected by conventional methods such as mammography for breast cancer patients, or X-rays for lung cancer patients. While mammography can detect tumors having approximately $2 \times 10^8$ cells, the methods of the present invention should enable detection of circulating cancer cells from tumors approximating this size or smaller.

The term "enrichment" as used herein refers to the process of substantially increasing the ratio of target bioentities (e.g., tumor cells) to non-target materials in the processed analytical sample compared to the ration in the original biological sample. In cases where peripheral blood is used as the starting materials, red cells are not counted when assessing the extent of enrichment. Using the method of the present invention, circulating epithelial cells may be enriched relative to leucocytes to the extent of at least 2,500 fold, more preferably 5,000 fold and most preferably 10,000 fold.

The terms "anti-coagulant" or "anti-coagulating agent" may be used interchangeably, and refer to compositions that are added to biological specimens for the purpose of inhibiting any undesired natural or artificial coagulation. An example of coagulation is blood clotting and common anti-coagulants are chelating agents, exemplified by ethylenediamine tetraacetic acid (EDTA), diethylenetriamine pentaacetic acid (DTPA), 1,2-diaminocyclohexane tetraacetic acid (DCTA), ethylenebis(oxyethylenenitrilo) tetraacetic acid (EGTA), or by complexing agents, such as heparin, and heparin species, such as heparin sulfate and low-molecular weight heparins. This may be further collectively defined as "clumping" or "clump formation". However, such clumps must be differentiated from "clusters" or aggregates of CTC that are counted as a single, intact CTC if they meet the classification criteria for intact CTC.

Clusters of CTC are believed to have greater proliferative potential than single CTC and their presence is thus diagnostically highly significant. One possible cause for an incrased propensity to establish secondary metastatic tumor sites may be the virtue of their adhesiveness. An even more likely cause is the actual size of a CTC cluster; larger clusters will become lodged in small diameter capillaries or pores in bone. Once there, the viability of the cells in the cluster would determine the chance of survivability at the new metastatic site.

The ideal "stabilizer" or "preservative" (herein used interchangeably) is defined as a composition capable of preserving target cells of interest present in a biological specimen, while minimizing the formation of interfering aggregates and cellular debris in the biological specimen, which in any way can impede the isolation, detection, and enumeration of targets cells, and their differentiation from non-target cells. In other words, when combined with an anti-coagulating agent, a stabilizing agent should not counteract the anti-coagulating agent's performance. Conversely, the anti-coagulating agent should not interfere with the performance of the stabilizing agent. Additionally, the disclosed stabilizers also serve a third function of fixing, and thereby stabilizing, permeabilized cells, wherein the expressions "permeabilized" or "permeabilization" and "fixing", "fixed" or "fixation" are used as conventionally defined in cell biology. The description of stabilizing agents herein implies using these agents at appropriate concentrations or amounts, which would be readily apparent to one skilled in cell biology, where the concentration or amount is effective to stabilize the target cells without causing damage. One using the compositions, methods, and apparatus of this invention for the purpose of preserving rare cells would obviously not use them in ways to damage or destroy these same rare cells, and would therefore inherently select appropriate concentrations or amounts. For example, the formaldehyde donor imidazolidinyl urea has been found to be effective at a preferred concentration of 0.1-10%, more preferably at 0.5-5% and most preferably at about 1-3% of the volume of said specimen. An additional agent, such as polyethylene glycol has also been found to be effective, when added at a preferred concentration of about 0.1% to about 5%, more preferably about 0.1% to about 1%, and most preferably about 0.1% to about 0.5% of the specimen volume.

A stabilizing agent must be capable of preserving a sample for at least a few hours. However, it has been shown that samples can be stabilized for at least up to 72 hours. Such long-term stability is important in cases where the sample is obtained in a location that is distant to the location where processing and analysis will occur. Furthermore, the sample must be stabilized against mechanical damage during transport.

Stabilizing agents are necessary to discriminate between in vivo tumor cell disintegration and disintegration due to in vitro sample degradation. Therefore, stabilizing agent compositions, as well as methods and apparatus for their use, are described in a co-pending application entitled "Stabilization of cells and biological specimens for analysis." That commonly owned application is incorporated by reference herein.

The terms "obvious cells" or "intact cells" may be used interchangeably, and refer to cells found during imaging analysis that contain nucleic acid and cytokeratin. These cells are usually visually round or oval, but may sometimes be polygonal or elongated. The nucleic acid area (i.e. labeled by nucleic acid dye) is smaller than the cytoplasmic area (i.e. labeled by anti-cytokeratin), and is surrounded by the cytoplasmic area.

The terms "suspicious cells", "suspect cells", or "fragments" may be used interchangeably, and refer to cells found during imaging analysis that resemble intact cells, but are not as visually distinct as intact cells. Based on imaging analysis, there are a number of possible types of suspect cells, including:

1. Enucleated cells, which are shaped like obvious cells, are positively stained for cytokeratin, but negative for nucleic acid;
2. Speckled or punctate cells, which are positively stained for nucleic acid, but have irregularly-stained cytokeratin; and
3. Amorphic cells, which stain positively for cytokeratin and nucleic acid, but are irregular in shape, or unusually large.

These suspicious cells are of interest in this invention because they may give additional information to the nature of the CTC, as well as the patient's disease. It is possible that staining or image artifacts may be observed during analysis. For example, enucleated cells sometimes appear to have a "ghost" region where the nucleus should have stained, but the corresponding region is nucleic acid negative. This may be caused by a number of external factors, including the labeling or imaging techniques. Also, cells have been observed with "detached" nuclei. While this may possibly indicate a cell releasing its nucleus, it is more likely that this appears due to an artifact of the imaging system. However, such "artifacts," when real, give valuable information about what may be happening to the intact cells. Therefore, as part of this invention, suspicious cells will be more closely analyzed.

Cell fragments are different than "debris" in that debris does not necessarily resemble a cell. The term debris as used herein, refers to unclassified objects that are specifically or non-specifically labeled during processing, and are visible as images during analysis, but are distinct from intact suspect cells. For example, it has been observed that damaged cells will release nuclear material. During processing, this nuclear material may be non-specifically magnetically labeled, and subsequently labeled with the nucleic acid stain. During analysis, the magnetically labeled and stained nuclear material can be observed. There are other objects that are similarly magnetically selected and stained which appear during analysis that are classified as debris.

The term "morphological analysis" as used herein, refers to visually observable characteristics for an object, such as size, shape, or the presence/absence of certain features. In order to visualize morphological features, an object is typically non-specifically stained. The term "epitopical analysis" as used herein, refers to observations made on objects that have been labeled for certain epitopes. In order to visualize epitopic features, an object is typically specifically stained or labeled. Morphological analysis may be combined with epitopical analysis to provide a more complete analysis of an object.

The importance of further visual observation is apparent when fragments and debris are often classified as "Not Assigned Events," or "Unassigned events". These terms arise from non-visual analysis, such as with flow cytometry. Because flow cytometry does not image objects, any event not falling in the specified populations that meet the criteria for the target cells, or the non-target cells (as is the case when non-specifically carried over WBC are negatively labeled), will fall outside either of these populations. However, as will be apparent throughout this specification, these unassigned events are important.

Figure 1B:
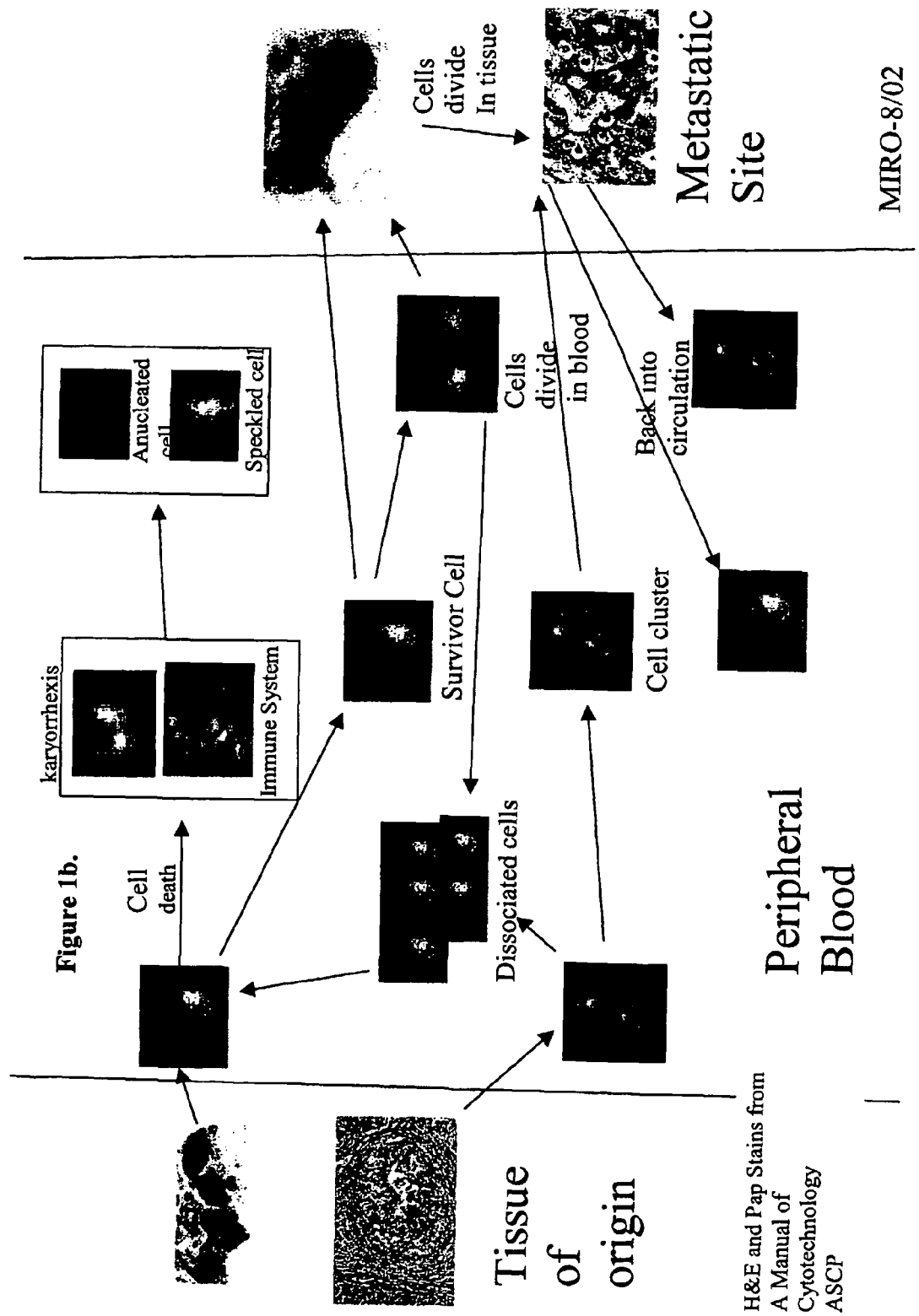

FIG. 1 is a model of various CTC stages, including shedding and metastasis. FIG. 1a shows these stages for cells, clusters, fragments, and debris. FIG. 1b shows actual images from samples at these same stages. The images of cells clusters, fragments, and debris were taken from CELLSPOTTER analyses of patient samples. The images of tissue samples (Origin and Metastatic sites) were taken from elsewhere (Manual of Cytology, American Society of Clinical Pathologists Press. 1983).

Briefly, a single cell sheds from a primary tumor into the blood. This cell either survives or dies in blood. If it survives, it may possibly divide in blood, or colonize at a secondary site. If the cell dies, depending on the method, the cell degrades into various types of fragments or debris. Another possibility is a cluster of cells is shed from a primary tumor into the blood, where it may dissociate into single cells, or remain intact, and colonize at a secondary site. If the cluster dissociates, it can behave similar to the single cell described above. If the cluster remains intact, it is more likely to form a secondary colony for the reasons described above, which includes the large diameter cluster becoming lodged in a small diameter capillary. Once lodged, if the cells are viable, the cluster would form a new tumor.

The presence of fragments and debris with very few intact cells suggests that there will be little chance of metastasis. Fragmented cells will not divide, and cannot form secondary tumors. Indeed, only intact CTC or possibly CTC clusters would be capable of colonizing secondary sites. Identification of antigens that play a role in the adhesion and penetration process may help. Follow up and assessment of metastatic sites of the patients with and without clusters will also provide further insight. Nuclear morphology is used to determine the activity status and abnormality of a cell. Chromatin clumping, the presence or absence of nucleoli, and hyperchromasia, are criteria used to determine whether a cell is benign or malignant, reacting to an immune response, or reacting to treatment. The cytoplasmic morphology is used to determine the level of differentiation (i.e. tissue of origin). For example, cytoplasmic morphology can classify cells as squamous versus glandular.

During blood draw and subsequent specimen processing, the surviving battered tumor cells present in the peripheral circulation may be further stressed and damaged by turbulence during blood draw into an evacuated tube and by specimen processing, e.g. transport of the blood tube and mixing prior to analysis. Such mechanical damage is additional to on-going immunological, apoptotic, and necrotic in processes leading to destruction of CTC that occur in vitro in a time dependent manner. We have found that the longer the specimen is stored, the greater the loss of CTC, and the larger the amounts of interfering debris and/or aggregates. Indeed, data presented in this specification (FIGS. 2 and 3) show dramatic declines in CTC counts in several blood specimens stored at room temperature or for 24 hrs or longer, indicating substantial in vitro destruction of CTC after blood draw. While the losses of hematopoietic cells are well known phenomena and the subject of above-cited patents by Streck Labs and by others, the occurrence of mechanical damage due to mixing or transport have to date not been recognized factors in the loss of CTC or rare cells. The formation of cellular debris and the interfering effects of accumulating debris and/or aggregates in the analysis of CTC or other rare cells have similarly been unrecognized to date. It appears to be most evident and problematic in highly sensitive enrichment assays requiring processing of relatively large blood volumes (5-50 mL), and subsequent microscopic detection or imaging of target cells after volume reduction (less than 1 mL). Such debris are either not normally seen, or do not interfere in conventional non-enrichment assays, for example, by flow cytometry or in enrichment by density gradients methods.

To explore if these damaged epithelial cells and epithelial cell fragments observed in patients could be caused by apoptosis of tumor cells induced by chemotherapy, a model to mimic tumor cell death was developed. Cells of the prostate cell line LnCaP were cultured with or without paclitaxel and spiked into blood of healthy donors. The immunomagnetically selected cells of the paclitaxel treated samples analyzed by CELLSPOTTER, an image analysis device, resembled those observed in the patient blood samples. Cells treated with paclitaxel displayed signs of apoptosis. The punctate cytokeratin staining pattern of the cells appear to correspond with a collapse of the cytoskeletal proteins (FIG. 4B vs. 6B). The initiating event in the sequence resulting from the microtubule stabilizing effects of paclitaxel which in turn may activate the pro-apoptotic gene Bim that senses cytoskeletal distress. Further evidence of caspase-cleaved cytokeratin resulting from apoptosis was obtained with the M30 Cytodeath antibody (Roche Applied Science, Manheim, Germany) that recognizes an epitope of cytokeratin 18 that is only exposed following caspase cleavage in early apoptosis. Only the paclitaxel treated LnCaP cells stained with M30 and most of the dimmer cytokeratin cells stained with M30, which would be consistent with cells undergoing apoptosis.

It should be noted that a number of different cell analysis platforms can be used to identify and enumerate cells in the enriched samples. Examples of such analytical platforms are CELLSPOTTER System, a magnetic cell immobilization and analysis system, using microscopic detection for manual observation of cells described in Example 2, and the CELLTRACKS™ system, a more advanced automatic optical scanning system. These two analytical platforms are described in U.S. Pat. Nos. 5,876,593; 5,985,153 and 6,136,182, each of which are incorporated by reference herein as disclosing the respective apparatus and methods for manual or automated quantitative and qualitative cell analysis.

Other analysis platforms include laser scanning cytometry (Compucyte), bright field base image analysis (Chromavision), and capillary volumetry (Biometric Imaging).

The enumeration of circulating epithelial cells in blood using the methods and compositions of a preferred embodiment of the present invention is achieved by immunomagnetic selection (enrichment) of epithelial cells from blood followed by the analysis of the samples. The immunomagnetic sample preparation is important for reducing sample volume and obtaining as much as a $10^4$ fold enrichment of the target (epithelial) cells. The reagents used for the multi-parameter flow cytometric analysis are optimized such that epithelial cells are located in a unique position in the multidimensional space created by the listmode acquisition of two light scatter and three fluorescence parameters. These include 1. an antibody against the pan-leukocyte antigen, CD45 to identify leukocytes (non-tumor cells);
2. a cell type specific or nucleic acid dye which allows exclusion of residual red blood cells, platelets and other non-nucleated events; and
3. a biospecific reagent or antibody directed against cytokeratin or an antibody having specificity for an EpCAM epitope whichi differs from that used to immunomagnetically select the cells.

It will be recognized by those skilled in the art that the method of analysis of the enriched tumor cell population will depend on the intended use of the invention. For example, in screening for cancers or monitoring for recurrence of disease, as described hereinbelow, the numbers of circulating epithelial cells can be very low. Since there is some "normal" level of epithelial cells, (very likely introduced during venipuncture), a method of analysis that identifies epithelial cells as normal or tumor cells is desirable. In that case, microscopy based analyses may prove to be the most accurate. Such examination might also include examination of morphology, identification of known tumor diathesis associated molecules (e.g., oncogenes).

Patients

Patients' age range was 47-91 year (mean 74), with initial diagnosis 2 to 10 years prior to study. Medical records were reviewed for therapy and stage. Patients and healthy volunteers signed an informed consent under an approved research study. Blood was drawn into 10 ml EDTA Vacutainer tubes (Becton-Dickinson, N.J.). Samples were kept at room temperature and processed within 6 hours after collection unless indicated otherwise.

Sample Preparation

Magnetic nanoparticles labeled with monoclonal antibodies identifying epithelial cell adhesion molecule (EpCAM) were used to label and separate by magnetic means epithelial cells from hematopoietic cells, as taught in commonly-owned U.S. Pat. No. 6,365,362, and U.S. patent application Ser. No. 10/079,939, filed 19 Feb. 2002, both of which are fully incorporated by reference herein. The magnetically captured cells resuspended in a volume of 2001 μl are fluorescently labeled to differentiate between hematopoietic and epithelial cells. A monoclonal antibody that recognizes keratins 4, 5, 6, 8, 10, 13, and 18, conjugated to Phycoerythrin (CK-PE) was used to identify epithelial cells and a monoclonal antibody that recognizes CD45 was used to identify leukocytes and identify hematopoietic cells that non-specifically bind to cytokeratin.

For multicolor fluorescent microscopy (CELLSPOTTER, an image analysis device) analysis CD45 was conjugated to allophycocyanin (CD45-APC, Caltag, Calif.) whereas for flow cytometric analysis perdinin chlorophyll protein conjugated CD45 (CD45-PerCP, BDIS San Jose, Calif.) was used. The nucleic acid specific dye DAPI (4,6-diamidino-2-phenylindole) was used to identify and visualize the nucleus with the CELLSPOTTER system and the nucleic acid dye used in the Procount system (BDIS, San Jose, Calif.) was used to identify cells by flow cytometry. After incubation, the excess staining reagents were aspirated and discarded and the captured cells were resuspended and transferred into a 12×75 mm tube for flow cytometric analysis or to a CELLSPOTTER analysis chamber (as described in U.S. application Ser. No. 10/074,900, filed 12 Feb. 2002, incorporated by reference herein) contained within a magnetic yoke assembly that holds the chamber between two magnets (Captivate, Molecular Probes, OR).

EXAMPLE 1

Sample Analysis Via Flow Cytometry

Samples were analyzed on a FACSCalibur flow cytometer equipped with a 488 nm argon ion laser (BDIS, San Jose, Calif.). Data acquisition was performed with CELLQUEST analysis system (BDIS, San Jose, Calif.) using a threshold on the fluorescence of the nucleic acid dye. The acquisition was halted after 8000 beads or 80% of the sample was analyzed. Multiparameter data analysis was performed on the listmode data (Paint-A-Gate$^{Pro}$, BDIS, San Jose, Calif.). Analysis criteria included size defined by forward light scatter, granularity defined by orthogonal light scatter, positive staining with the PE-labeled anti-cytokeratin MAb and no staining with the PerCP-labeled anti-CD45 Mab. For each sample, the number of events present in the region typical for epithelial cells was multiplied by 1.25 to account for the sample volume not analyzed by flow cytometry.

Figure 2:
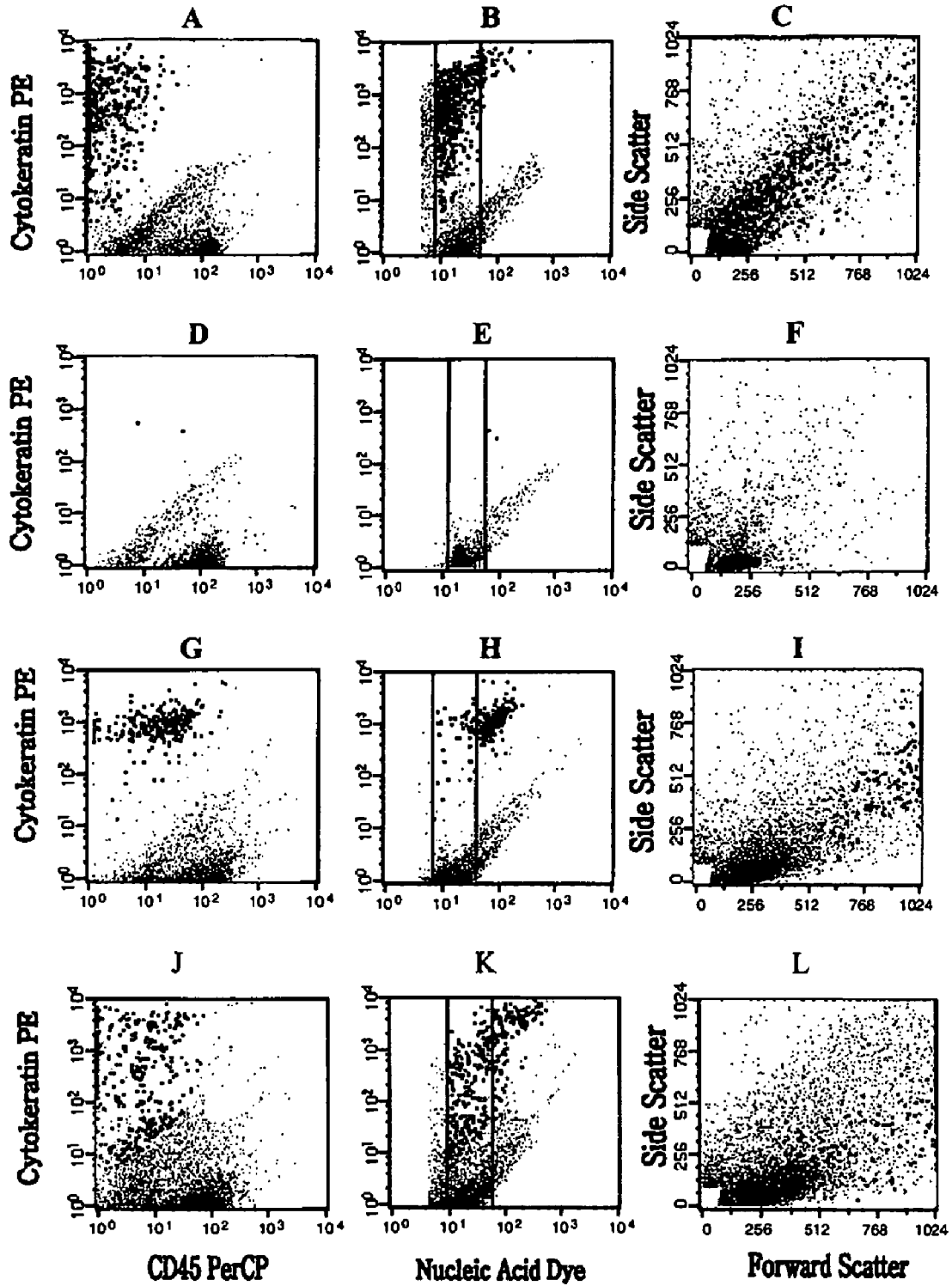
FIG. 2—Flow cytometric analysis of immunomagnetically enriched tumor cells from 7.5 ml blood.

FIG. 2 Panels A, B and C shows the flow cytometric analysis of a blood sample of a patient with metastatic prostate cancer. Two vertical lines in Panel B illustrate the low and high boundary of nucleic acid (NAD) content of leukocytes (red dots). CTC candidates express Cytokeratin (CK+), lack CD45 (CD45−) and contain nucleic acids (NAD+). CTC candidates having NAD equal or higher than leukocytes are considered cells and are depicted black. CK+, CD45− events with NAD content less than leukocytes were not considered cells and depicted blue. The blue events were clearly smaller as compared with the black colored CTC as evident by the smaller forward light scatter signals. The threshold on the NAD staining intensity clearly excluded a large portion of CK+, CD45− events with even lower NAD staining intensity. In analysis of blood samples from healthy donors few such CK+, CD45− events are observed suggesting that this phenomenon is related to cancer. A typical example of an analysis of a blood sample from a healthy donor is shown in FIGS. 2D, 2E, and 2F.

EXAMPLE 2

Sample Analysis Via CellSpotter®

The CELLSPOTTER system consists of a microscope with a Mercury Arc Lamp mercury arc lamp, a 10× objective, a high resolution X, Y, Z stage and a-four filter cube changer. Excitation, dichroic and emission filters in each of four cubes were for DAPI 365 nm/400 nm/400 nm, for DiOC16 480 nm/495 nm/510 nm, for PE 546 nm/560 nm/580 nm and for APC 620 nm/660 nm/700 nm. Images were acquired with a digital camera connected to a digital frame grabber. The surface of the chamber is 80.2 mm$^2$ and 4 rows of 35 images for each of the 4 filters resulting in 560 images have to be acquired to cover the complete surface. The CELLSPOTTER acquisition program automatically determines the region over which the images are to be acquired, the number of images to acquire, the position of each image and the microscope focus to use at each position. All the images from a sample are logged into a directory that is unique to the specific sample identification. An algorithm is applied on all of the images acquired from a sample to search for locations that stain for DAPI and CK-PE. If the staining area is consistent with that of a potential tumor cell (DAPI+, CK-PE+) the software stores the location of these areas in a database. The software displays thumbnails of each of the boxes and the user can confirm that the images represented in the row are consistent with tumor cells, or stain with the leukocyte marker CD45. The software tabulates the checked boxes for each sample and the information is stored in the database.

Figure 3:
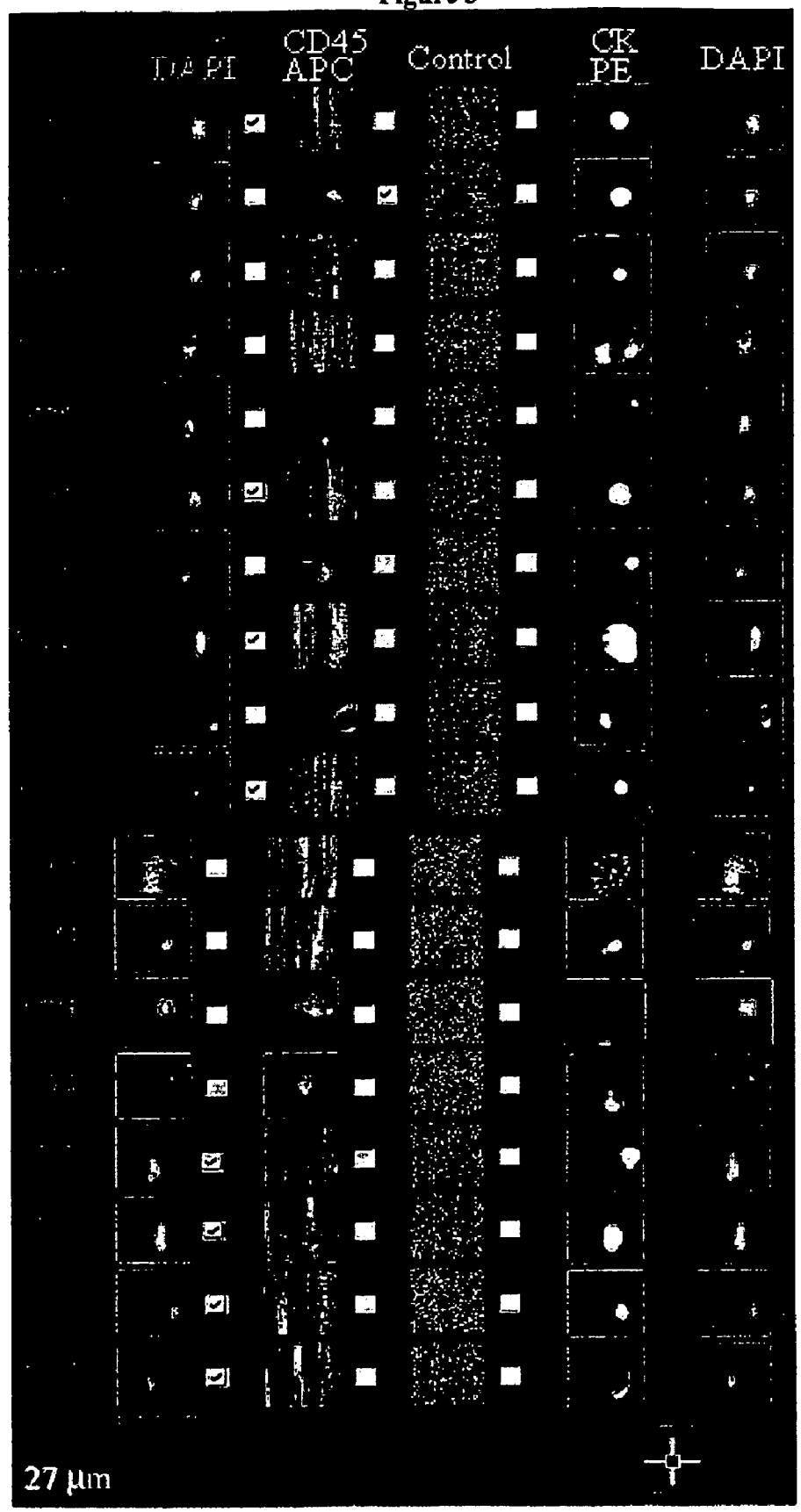
FIG. 3—CELLSPOTTER analysis of a 7.5ml blood sample from a metastatic prostate cancer patient that was immunomagnetically enriched for tumor cells. The lines of thumbnails correspond to the different dyes used in the staining process showing tumor candidates stained with cytokeratin PE (green) and DAPI (magenta).

FIG. 3 shows examples of CELLSPOTTER analysis of a blood sample from a patient with metastatic prostate cancer. Regions that potentially contain tumor cells are displayed in rows of thumbnails. The ruler in the left lower corner of the figure indicates the sizes of the thumbnails. From right to left these thumbnails represent nuclear (DAPI), cytoplasmic cytokeratin (CK-PE), control cell (DiOC$_{16}$(3)) and surface CD45 (CD45-APC) staining. The composite images shown at the left show a false color overlay of the purple nuclear (DAPI) and green cytoplasmic (CK-PE) staining. The check box beside the composite image allow the user to confirm that the images represented in the row are consistent with tumor cells and the check box beside the CD45-APC image is to confirm that a leukocyte or tumor cell stain non-specifically. In this patient sample, the software detected 2761 rows of thumbnails that demonstrated staining consistent with tumor cells. Eighteen of the 2761 rows are shown in the figure labeled 1631-1640 and 1869-1876. Rows numbered 1631, 1636, 1638, 1640, and 1873-1876 are checked off and display features of CTC defined as a size greater than 4 μm, the presence of a nucleus surrounded by cytoplasmic cytokeratin staining and absence of DiOC$_{16}$(3) and CD45 staining. Note the difference in appearance of the tumor cells: the cell in row 1638 is large and the one in row 1640 is significantly smaller. The immunophenotype of the events in rows 1634 and 1869 are consistent with tumor cells but their morphology is not consistent with intact cells. The thumbnail in row 1869 shows a large nucleus and speckled cytoplasmic due to retraction of cytoskeletal proteins consistent with apoptosis of the cell. The thumbnail in row 1634 shows a damaged cell that appears to extrude its nucleus. The thumbnail shown in row 1632 shows a cell that stains both with cytokeratin as well as CD45 and is either a tumor cell non-specifically binding to CD45 or a leukocyte non specifically staining with cytokeratin. In this instance the morphology of the cell closely resembles that of a lymphocyte. The thumbnails shown in rows 1633, 1635, 1637, 1639, 1870 and 1872 shows cytokeratin staining objects that are larger that 4 µm but have no resemblance to cells. The cytokeratin staining objects in thumbnails 1637, 1639 and 1872 are in close proximity of a leukocyte.

Figure 4:
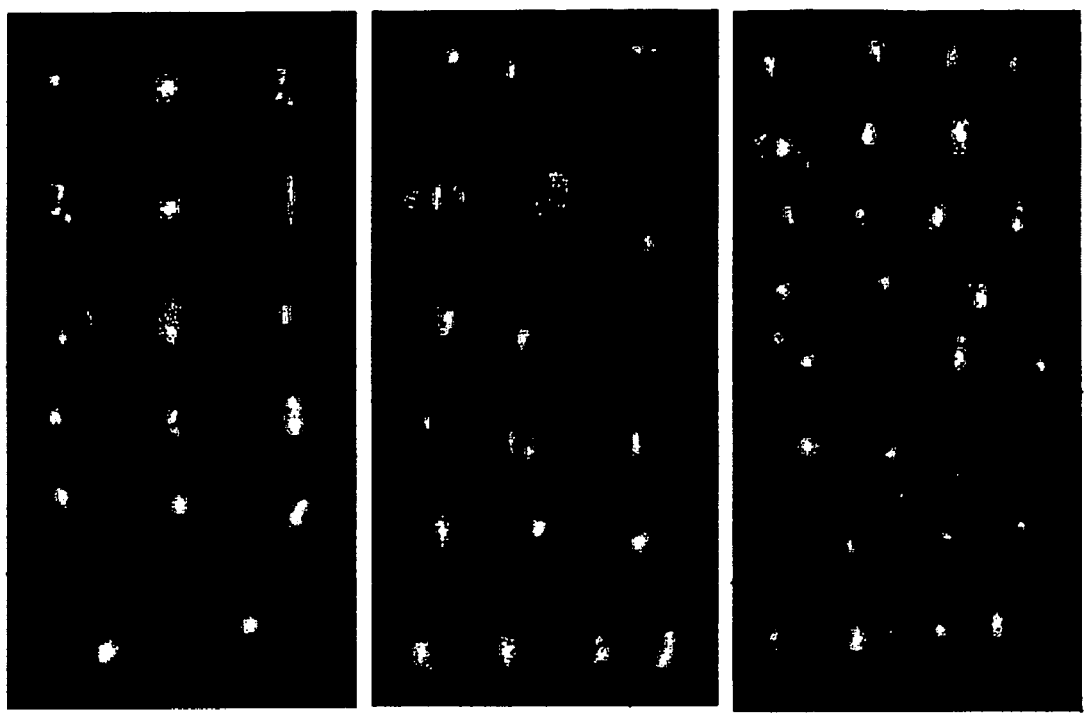
FIG. 4—CELLSPOTTER classifications of tumor cells isolated from a single whole blood sample of a patient with metastatic prostate cancer stained with cytokeratin PE (green) and DAPI (magenta).
A—intact cells
B—damaged tumor cells
C—tumor cell fragments FIG. 5—A comparison of the number of obvious CTC to suspect CTC in 20 clinical samples.

Based on observation of images of CTC candidates in several patient samples, CTC were classified into three categories: intact CTC, damaged CTC, and CTC fragments all not staining with CD45 and not appearing in the $DiOC_{16}(3)$ filter. FIG. 4 displays examples of the three categories of CTC isolated from a single tube of blood of a patient with metastatic prostate cancer undergoing therapy. Intact tumor cells shown in FIG. 3A were defined as objects larger than 4 µm with a relatively smooth cytoplasmic membrane, cytoskeletal proteins throughout the cytoplasm, and an intact nucleus encompassed within the nucleus. Damaged CTC shown in FIG. 4B were defined as objects larger than 4 µm with speckled cytokeratin staining or ragged cytoplasmic membrane, and a nucleus associated with the cytokeratin staining. Tumor cell fragments shown in FIG. 4C were defined as round cytokeratin staining objects larger than 4 µm with or without association of nuclear material that had no morphological resemblance to a cell.

EXAMPLE 3

CTC in Prostate Cancer Patients

CTC were enumerated in 18 blood samples of prostate cancer patients and 27 samples from healthy individuals by both flow cytometry and CELLSPOTTER system. The results shown in Table 1 were sorted by increasing number of intact CTC detected by the CELLSPOTTER system.

TABLE 1

Enumeration of CTC by the CELLSPOTTER system and flow cytometry in 18 blood samples of prostate cancer patients and 27 samples from healthy individuals.

| | CellSpotter ® | | | | | | Flow Cytometry |
|---|---|---|---|---|---|---|---|
| Patient | Intact Tumor Cells | | Damaged Tumor Cells | | Tumor Cell Fragments | | CK+CD45-NA+ |
| Sample | # | % | # | % | # | % | # |
| 1 | 0 | 0 | 1 | 50 | 1 | 50 | 5 |
| 2 | 0 | 0 | 2 | 100 | 0 | 0 | 12 |
| 3 | 0 | 0 | 2 | 66 | 1 | 34 | 1 |
| 4 | 0 | 0 | 2 | 50 | 2 | 50 | 0 |
| 5 | 0 | 0 | 2 | 29 | 5 | 71 | 5 |
| 6 | 0 | 0 | 3 | 60 | 2 | 40 | 18 |
| 7 | 0 | 0 | 3 | 38 | 5 | 62 | 0 |
| 8 | 0 | 0 | 7 | 44 | 9 | 56 | 10 |
| 9 | 0 | 0 | 13 | 76 | 4 | 24 | 2 |
| 10 | 1 | 5 | 1 | 5 | 20 | 90 | 4 |
| 11 | 1 | 10 | 4 | 40 | 5 | 50 | 0 |
| 12 | 2 | 22 | 1 | 11 | 6 | 67 | 4 |
| 13 | 28 | 6 | 7 | 1 | 441 | 93 | 69 |
| 14 | 70 | 5 | 168 | 12 | 1204 | 83 | 683 |
| 15 | 322 | 3 | 448 | 13 | 4244 | 87 | 500 |
| 16 | 350 | 5 | 112 | 2 | 5924 | 93 | 723 |
| 17 | 350 | 2 | 1429 | 9 | 14412 | 89 | 2420 |
| 18 | 742 | 17 | 112 | 2 | 3641 | 81 | 310 |
| Mean | — | 4% | — | 34% | — | 62% | — |
| 27 samples from healthy donors | | | | | | | |
| Mean | 0.04 | | 0.96 | | 4.96 | | 0.7 |
| SD | 0.19 | | 1.85 | | 3.98 | | 1.14 |

TABLE 1-continued

Enumeration of CTC by the CELLSPOTTER system and flow cytometry in 18 blood samples of prostate cancer patients and 27 samples from healthy individuals.

| | CellSpotter ® | | | | | | Flow Cytometry |
|---|---|---|---|---|---|---|---|
| Patient | Intact Tumor Cells | | Damaged Tumor Cells | | Tumor Cell Fragments | | CK+CD45-NA+ |
| Sample | # | % | # | % | # | % | # |
| Min | 0 | | 0 | | 0 | | 0 |
| Max | 1 | | 7 | | 15 | | 4 |

\# - number CTC in 7.5 ml blood
% - percentage of all CTC detected by CellSpotter ®

In the CELLSPOTTER analysis, the proportion of intact CTC clearly constituted the smallest fraction of CTC and ranged from 0% to 22% of all CTC (mean 4%). The proportion of damaged CTC ranged from 1% to 100% (mean 34%) and the CTC fragments constituted the largest portion of CTC ranging from 0% to 93% (mean 62%). The distribution of CTC over the three categories between the patients varied considerably as amplified by a lack of correlation between intact CTC and damaged CTC ($R^2$=0.20) and intact CTC and CTC fragments ($R^2$=0.42) and some correlation between damaged CTC and CTC fragments ($R^2$=0.88). Comparison of intact CTC by CELLSPOTTER analysis and CTC enumerated by flow cytometry showed no significant correlation ($R^2$=0.26) whereas significant correlations were found between the damaged CTC and CTC by flow cytometry ($R^2$=0.92) and CTC fragments and CTC by flow cytometry ($R^2$=0.93). Comparison of the CTC detected by flow cytometry and the CELLSPOTTER system suggests that CTC detected by flow cytometry encompass intact CTC as well as damaged CTC and to a certain extent, CTC fragments.

EXAMPLE 4

Mimicking Cell Damage by in-vitro Induction of Apoptosis in LnCaP Cells

Figure 6:
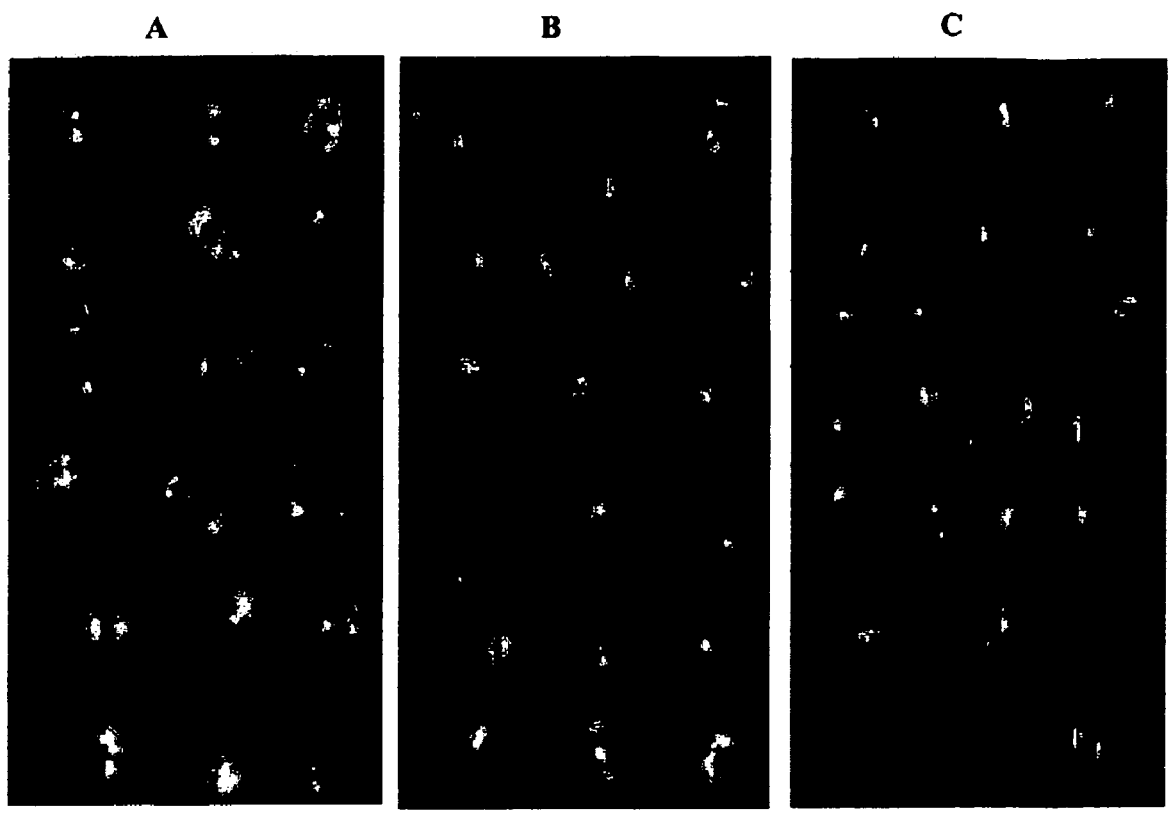
FIG. 6—CELLSPOTTER classifications of paclitaxel treated LnCaP cells spiked into whole blood and isolated then stained with cytokeratin PE (green) and DAPI (magenta).
A—intact cells
B—dying tumor cells
C—tumor cell fragments

To investigate the effect of apoptosis induced by cytotoxic agents on flow cytometric and CELLSPOTTER analysis of CTC, cells from the prostate cell line LnCaP were cultured in the presence or absence of 40 nM paclitaxel for 72 hours. Following incubation, untreated LnCaP cells demonstrated a viability of >95% by trypan blue exclusion and 33% for the paclitaxel treated cells. The treated and untreated LnCaP cells were spiked into blood of healthy donors, selected by the ferrofluid methods described above, and analyzed by the CELLSPOTTER system. In experiments in which LnCaP cells were spiked into blood that were not treated with paclitaxel greater than 95% of the LnCaP cells were classified as intact tumor cells. The morphologic appearance of the paclitaxel treated LnCaP cells showed close resemblance to that of the CTC observed in the patient samples and are shown in FIG. 6. Intact LnCaP cells that survived paclitaxel treatment are shown in FIG. 6A, damaged LnCaP, of which the majority show speckled cytokeratin staining, are shown in FIG. 6B, and tumor fragments are shown in FIG. 6C.

Normal blood samples spiked with paclitaxel treated and untreated LnCaP cells were also prepared for flow cytometric analysis. In FIGS. 2G, 2H, and 2I, the flow cytometric analysis of a blood sample spiked with 501 LnCaP cells is shown. A predominantly bright cytokeratin positive population with a nucleic acid content greater than normal human leukocytes and relatively large size as illustrated by the large forward light scatter signals is shown and depicted black in the figure. Only few CK+, CD45– events with NAD content less than leukocytes and depicted blue are detected in the sample. FIGS. 2J, 2K, and 2L shows the flow cytometric analysis of paclitaxel treated LnCaP cells spiked in blood. In contrast to viable LnCaP cells, a wide distribution of cytokeratin staining was observed with a significant portion of the population demonstrating a decreased concentration of nucleic acid content. In addition, numerous small cytokeratin positive events with less nucleic acid content as leukocytes were observed. The pattern of the patient closely resembled that of the pattern of the paclitaxel treated LnCaP cells supporting the hypothesis that the CTC detected by flow cytometry represent intact CTC as well as a variety of disintegrating cells in blood of cancer patients.

The data shown above demonstrate that in the blood of patients with prostate cancer, CTC detected by both flow cytometry and CELLSPOTTER system are comprised of intact cells and a variety of disintegrated cells. The apoptosis induced in vitro by paclitaxel suggests that the detected CTC in patient blood samples are undergoing apoptosis, necrosis, or in vivo damage to a varying degree caused by the treatment, mechanical damage by passage through the vascular system, or by the immune system.

Another source of cell disintegration caused in vitro could, however, be introduced by the sample preparation or the lack of stability of CTC or other blood components after blood draw. To investigate the effect of sample aging, blood samples drawn from 12 patients with prostate cancer were processed and analyzed by flow cytometry within two hours, after 24 hours, and after 6 and 18 hours if sufficient blood was available. In 8 of the 12 patient samples, CTC were detected at a level greater than the mean+3SD of that detected in normal donors. As shown in Table 2, a loss of CTC with sample aging was observed in all 8 samples.

TABLE 2

Enumeration of CTC by flow cytometry in 8 blood samples of prostate cancer patients processed and analyzed at different time points after blood draw

| | Time after blood draw | | | |
|---|---|---|---|---|
| Patient # | <2 hr #CTC | ~6 hr #CTC | ~18 hr #CTC | ~24 hr #CTC |
| 1 | 5 | — | — | 0 |
| 2 | 8 | 9 | 2 | 3 |
| 3 | 15 | — | — | 0 |
| 4 | 31 | — | — | 3 |
| 5 | 44 | — | — | 8 |
| 6 | 45 | — | — | 1 |
| 7 | 49 | 38 | 19 | 26 |
| 8 | 78 | — | — | 0 | hr = hours
CTC = number of CTC in 5 ml blood

Significant reductions in the number of CTC were detected when blood processing was delayed demonstrating the fragility of CTC, and making it necessary to process non-stabilized blood samples no later than six hours after blood draw to obtain accurate CTC counts. To reliably assess if clinically relevant information is contained within the different stages of tumor cell degradation, a blood preservative is needed that stabilizes CTC at the time of blood draw to obtain an accurate reflection of what is occurring inside the body. Furthermore, the sample preparation method for sensitive assays used to enrich for CTC requires that all classes of CTC are captured, and therefore excludes the use of traditional density gradient separation methods in the prior art.

EXAMPLE 5

Obvious CTC and Suspect CTC are Important Indicators

It is important to be able to distinguish between in vivo and in vitro damage for sensitive assays, such as those described here. This is especially evident when the assay attempts to determine the effectiveness of treatments or therapies, which are known to cause in vivo cellular damage. If sample handling, processing, or analysis were to result in damaging the target cells, forming suspect cells, fragments, or debris, the assay will not give meaningful results.

An assay was developed to directly detect CTC in 100 μl of blood without any enrichment method with a flow cytometer. The 100 μl assay detects only EpCAM positive cells and the sensitivity is very low. However, some advanced stage cancer patients with high CTC counts are expected to be observable. This assay should give a reliable confirmatory estimation of CTC because it is a direct assay that involves no manipulation. Data was generated with several patient samples using the assay to answer several questions.

The 100 μl assay categorizes cells based on properties such as size and staining intensity. Obvious CTC have bright nucleic acid staining (similar to leukocytes), positive EpCAM antigen staining and size similar to leukocytes or larger. Suspect CTC are any objects positive for EpCAM antibody but not characterized as obvious CTC (i.e. dim nucleic acid, size smaller than leukocytes). The assay identifies objects from both categories.

Figure 5:
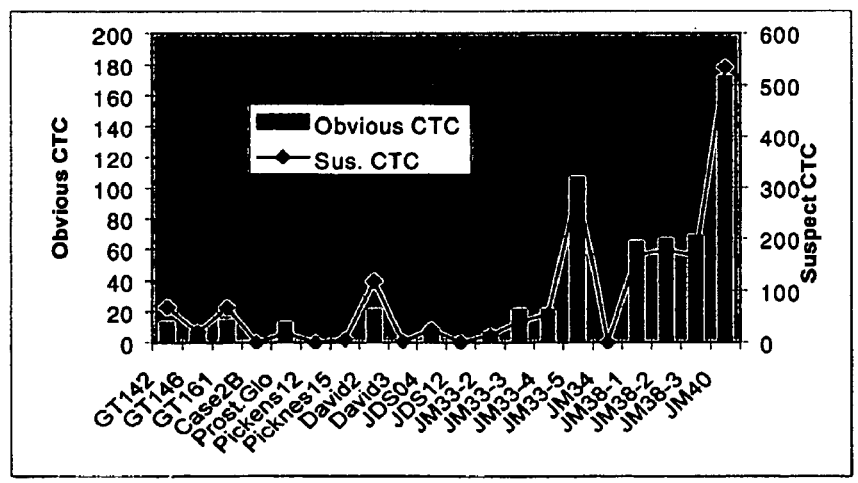

FIG. 5 shows the presence of obvious and suspect CTC in blood as determined by the 100 μl assay. The suspect CTC are not created during sample processing (in vitro damage) as the 100 μl assay is a direct assay and does not involve any separation or wash steps. The data above also show there is a relationship between the number of obvious and suspect CTC. The number of suspect CTC seems to increase as the number of obvious CTC increases. When the numbers of suspect versus obvious CTC is plotted, the slope of 2.92 indicates the proportion of suspect CTC present in sample when compared to obvious CTC. The correlation coefficient of $r^2=0.97$ shows an excellent correlation between obvious CTC and suspect CTC for a number of clinical samples. In addition, suspect CTC are also seen in the ferrofluid-selection assay, and have properties similar to suspect CTC detected in the blood by the direct assay. It is important to include suspect CTC in addition to obvious CTC in total tumor cell count.

An important question is how the data from the 100 μl assay compares with ferrofluid-selected CTC (enriched CTC). Does the assay quantitatively detect CTC? Another question is what is the recovery of CTC in the ferrofluid-selected assay if the flow assay data is correct. Three main factors determining the recovery of CTC in the 100 μl assay are:
  EpCAM density,
  cytokeratin positivity, and
  nucleus positivity.

The suspect CTC have lower EpCAM density compared to obvious CTC and significance of this is not yet well known.

A comparison was made of obvious and suspect CTC by the 100 μl assay to the ferrofluid-selection assay using 7 ml of blood. This data was obtained from a prostate patient samples and analyzed by flow cytometry. Both obvious and suspect CTC increased with storage time and the trend was similar to CTC detected in the ferrofluid-selection assay, thereby validating the 100 µl assay. The recovery of CTC from the ferrofluid-selection assay was about 90% based on the CTC in 100 µl of blood. It was also known that MFI (Mean Fluorescence Intensity which correlates the EpCAM density) of CTC from this patient was high (MFI=300), and all EpCAM positive cells are cytokeratin positive. However, the recoveries of CTC from some other clinical samples has been as low as 20%. There may be several factors that contribute for a lower recovery, such as EpCAM positive/cytokeratin negative cells, cytokeratin dim cells, and mucin on the cell surface inhibiting the ability of ferrofluid to bind cells.

The assay described herein was performed on patients at two times. Response was measured by bi-dimensional imaging of the lesion. The Ration (Ratio=Obvious CTC/Total CTC) is similar to the Response Index, described earlier, and can be used as a numeric indicator of treatment success. The results are summarized in Table 3. Ratios near 1.0 indicate the Total CTC are obvious CTC, and ratios near 0.0 indicate more suspect CTC or debris. Progression indicates the lesion is increasing in size, Partial Response indicates a response to treatment where the Ratio is relatively low, and stabilized indicates no change, or reduction in lesion size. A positive change indicates an increase in the number of intact CTC, corresponding to the progression of the disease. A negative change indicates a decrease in the number of intact CTC, or a possible increase in the number of suspect CTC and/or debris, corresponding to a response to treatment.

These results show the importance of including suspect CTC and debris when analyzing response to treatment because the numbers of intact or obvious CTC alone would not provide as much information. Furthermore, such indicators are useful for short-term monitoring of treatments and therapies, or longer term monitoring for remission and/or relaps.

TABLE 3

Obvious CTC and suspect CTC corresponding to a treatment response

| Response | Ratio1 | Ratio2 | Change |
|---|---|---|---|
| Progressive | 0.3 | 0.0 | −0.3 |
| | 0.0 | 0.0 | 0.0 |
| | 0.5 | 0.6 | 0.1 |
| | 0.9 | 1.0 | 0.1 |
| | 0.3 | 0.5 | 0.2 |
| | 0.4 | 0.7 | 0.3 |
| | 0.0 | 0.4 | 0.4 |
| | 0.5 | 0.9 | 0.4 |
| | 0.0 | 0.5 | 0.5 |
| | 0.0 | 0.6 | 0.6 |
| Partial Response | 1.0 | 0.0 | −1.0 |
| | 0.4 | 0.0 | −0.4 |
| | 0.3 | 0.0 | −0.3 |
| | 0.5 | 0.2 | −0.3 |
| | 0.4 | 0.3 | −0.1 |
| | 0.0 | 0.0 | 0.0 |
| | 0.3 | 1.0 | 0.7 |
| Stabilized | 1.0 | 0.0 | −1.0 |
| | 0.5 | 0.0 | −0.5 |
| | 1.0 | 0.7 | −0.3 |
| | 0.3 | 0.0 | −0.3 |
| | 0.4 | 0.3 | −0.1 |
| | 0.1 | 0.0 | −0.1 |
| | 0.2 | 0.1 | −0.1 |
| | 0.6 | 0.5 | −0.1 |
| | 0.9 | 0.8 | −0.1 |
| | 0.0 | 0.0 | 0.0 |
| | 0.6 | 0.7 | 0.1 |

TABLE 3-continued

Obvious CTC and suspect CTC corresponding to a treatment response

| Response | Ratio1 | Ratio2 | Change |
|---|---|---|---|
| | 0.6 | 0.8 | 0.2 |
| | 0.0 | 1.0 | 1.0 |

Enumeration of tumor cell debris may prove more significant in cancer diagnostics and therapeutics than detection of large proliferative cell clusters. Since debris particles in the size range, probably about 1-3 µm (the size of platelets), have been observed to be present in much larger amounts than intact cells, they may constitute a separate, independent, and possibly more sensitive marker than intact tumor cells. The presence of damaged CTC may be particularly relevant in detecting early-stage cancer when the immune system is intact and most active. Similarly, dramatic increases in debris during therapy may suggest breakdown of both circulating and tissue tumor cells (i.e. therapeutic effectiveness), paralleling the massive release of cellular components like calcium observed during tumor disintegration. Like soluble tumor markers, such debris may be detectable in blood without enrichment, or with minimal enrichment in the buffy coat layer and constitute an alternative, and potentially simpler diagnostic tool than intact cell enrichment/analysis. Since morphology is lost in CTC debris, detection could be done by flow cytometry as long as the debris is stained for the appropriate determinants, such as cytokeratin.

As previously discussed, damaged or fragmented CTC with or without DNA are theoretically to be expected, and therefore are not undesirable events in specimens from patients undergoing effective therapy and in untreated patients with strong immune systems. The ratio or % of intact CTC to total detectable events may prove to be a useful parameter to the clinician in assessing a patient's immune system or response to therapy. The normal immune defenses, especially activated neutrophils, also can damage or destroy CTC as foreign species by a process called "extracellular killing" even if the CTC are larger than the neutrophils. It does not seem surprising to find only a small percentage of the shed CTC as intact cells, unless the immune system is overwhelmed in the late stages of disease or therapy is ineffective.

Hence, there are a number of methods for in vitro cancer detection: conclusive detection of intact circulating cells/clusters, and inferential methods like circulating tumor debris (including total and tumor-specific RNA/DNA, and conventional soluble tumor markers). However, no method by itself may be sufficiently sensitive. Lower specificity of debris detection compared to CTC morphology may be a problem in screening that could be minimized (e.g. with triple labeling), but it may be a lesser problem in monitoring. Further statistical analysis and correlations on debris data relative to intact CTC and diagnostic stage in patients compared to normals appear worthwhile in assessing the sensitivity and specificity of debris analysis.

Examples of different types of cancer that may be detected using the compositions, methods and kits of the present invention include apudoma, choristoma, branchioma, malignant carcinoid syndrome, carcinoid heart disease, carcinoma e.g., Walker, basal cell, basosquamous, Brown-Pearce, ductal, Ehrlich tumor, in situ, Krebs 2, merkel cell, mucinous, non-small cell lung, oat cell, papillary, scirrhous, bronchiolar, bronchogenic, squamous cell and transitional cell reticuloendotheliosis, melanoma, chondroblastoma, chondroma, chondrosarcoma, fibroma, fibrosarcoma, giant cell tumors, histiocytoma, lipoma, liposarcoma, mesothelioma, myxoma, myxosarcoma, osteoma, osteosarcoma, Ewing's sarcoma, synovioma, adenofibroma, adenolymphoma, carcinosarcoma, chordoma, mesenchymoma, mesonephroma, myosarcoma, ameloblastoma, cementoma, odontoma, teratoma, throphoblastic tumor, adenocarcinoma, adenoma, cholangioma, cholesteatoma, cylindroma, cystadenocarcinoma, cystadenoma, granulosa cell tumor, gynandroblastoma, hepatoma, hidradenoma, islet cell tumor, leydig cell tumor, papilloma, sertoli cell tumor, theca cell tumor, leiomyoma, leiomyosarcoma, myoblastoma, myoma, myosarcoma, rhabdomyoma, rhabdomyosarcoma, ependymoma, ganglioneuroma, glioma, medulloblastoma, meningioma, neurilemmoma, neuroblastoma, neuroepithelioma, neurofibroma, neuroma, paraganglioma, paraganglioma nonchromaffin, antiokeratoma, angioma sclerosing, angiomatosis, glomangioma, hemangioendothelioma, hemangioma, hemangiopericytoma, hemangiosarcoma, lymphangioma, lymphangiomyoma, lymphangiosarcoma, pinealoma, carcinosarcoma, chondrosarcoma, cystosarcoma phyllodes, fibrosarcoma, hemangiosarcoma, leiomyosarcoma, leukosarcoma, liposarcoma, lymphangiosarcoma, myosarcoma, myxosarcoma, ovarian carcinoma, rhabdomyosarcoma, sarcoma (Kaposi's, and mast-cell), neoplasms (e.g., bone, digestive system, colorectal, liver, pancreatic, pituitary, testicular, orbital, head and neck, central nervous system, acoustic, pelvic, respiratory tract, and urogenital), neurofibromatosis, and cervical dysplasia.

However, the present invention is not limited to the detection of circulating epithelial cells and/or clusters, fragments, or debris only. For example, endothelial cells have been observed in the blood of patients having a myocardial infarction. Endothelial cells, myocardial cells, and virally infected cells, like epithelial cells, have cell type specific determinants recognized by available monoclonal antibodies. Accordingly, the methods and the kits of the invention may be adapted to detect such circulating endothelial cells. Additionally, the invention allows for the detection of bacterial cell load in the peripheral blood of patients with infectious disease, who may also be assessed using the compositions, methods and kits of the invention. It would be reasonable to expect that these rare cells will behave similarly in circulation, and that fragments and/or debris will be present in similar conditions as those described hereinabove.

The preferred embodiments of the invention as herein disclosed, are also believed to enable the invention to be employed in fields and applications additional to cancer diagnosis. It will be apparent to those skilled in the art that the improved diagnostic modes of the invention are not to be limited by the foregoing descriptions of preferred embodiments. Finally, while certain embodiments presented above provide detailed descriptions, the following claims are not limited in scope by the detailed descriptions. Indeed, various modifications may be made thereto without departing from the spirit of the following claims.

We claim:

1. A method for monitoring malignancy in a test subject comprising:
   a. obtaining a blood sample from a test subject, said sample comprising a mixed cell population suspected of containing intact malignant cancer cells of epithelial cell origin and further comprising:
      i. cell fragments derived from said malignant cells, and/or
      ii. cellular debris derived from said malignant cells;
   b. preparing a sample with magnetically-labeled said intact malignant cells, said cell fragments and said cellular debris wherein said blood sample is mixed with colloidal magnetic particles, having a size range between 90 to 150 nm and a bovine serum albumin coating using high temperature, coupled to a first biospecific ligand which reacts and binds specifically to an epitope present in each of said intact malignant cells, said cell fragments and said cellular debris to form specific binding complexes with said colloidal magnetic particles and first biospecific ligand;
   c. exposing said specific binding complexes formed in step b) to an externally-applied high gradient magnetic field to the substantial exclusion of other specimen components;
   d. contacting said specific binding complexes in step c) with at least one additional biospecific ligand forming a specific binding pair with a receptor of said intact malignant cells, said cell fragments and said cellular debris, to the substantial exclusion of other specimen components, wherein the receptor is present in malignant tumor cells of epithelial cell origin;
   e. differentially analyzing amounts of said labeled malignant cells, said labeled cell fragments and said labeled cellular debris in step d) over time, a change in the numerical proportions of said labeled malignant cells, said labeled cell fragments, and said labeled cellular debris indicating a change of malignancy.

2. The method of claim 1, wherein said is blood sample is whole blood sample.

3. The method of claim 2, wherein after said blood sample is obtained, it is contacted with an agent capable of stabilizing said blood sample.

4. The method of claim 1, wherein after the step of preparing said magnetically-labeled sample, said sample is subjected to a high gradient magnetic field to produce a separated magnetically-labeled fraction which is enriched for said intact malignant cells, and said cell fragments and said cellular debris.

5. The method of claim 1, wherein said analysis is selected from the group consisting of: multiparameter flow cytometry, immunofluorescent microscopy, laser scanning cytometry, bright field base image analysis, capillary volumetry, spectral imaging analysis, manual cell analysis, and automated cell analysis.

6. The method of claim 1, wherein said analysis further comprises classifying cell fragments or said cellular debris based on their origin as caused by apoptosis or necrosis and wherein said additional biospecific ligand is directed against cytokeratin.

7. The method of claim 6, wherein analysis further comprises classifying cell fragments or said cellular debris based on their origin as caused by mechanical damage, drug-induced damage, or immunological damage and wherein said additional biospecific ligand is directed against cytokeratin.

8. The method of claim 6, wherein said classification is based on at least one of the group consisting of: morphologic analysis and epitopic analysis.

9. A method for monitoring malignancy in a test subject comprising:
   a. obtaining a blood sample from a test subject, said sample comprising a mixed cell population suspected of containing intact malignant cancer cells of epithelial cell origin and clusters of said malignant cells;
   b. preparing a sample with magnetically-labeled said intact malignant cells and said clusters of malignant cells wherein said blood sample is mixed with colloidal magnetic particles, having a size range between 90 to 150 nm and a bovine serum albumin coating using high temperature, coupled to a first biospecific ligand which reacts and binds specifically to an epitope present in each of said intact malignant cells and said clusters of malignant cells to form specific binding complexes with said colloidal magnetic particles and first biospecific ligand;

c. exposing said specific binding complexes formed in step b) to an externally-applied high gradient magnetic field to the substantial exclusion of other specimen components;

d. contacting said specific binding complexes in step c) with at least one additional biospecific ligand forming a specific binding pair with a receptor of said intact malignant cells and said clusters of malignant cells, to the substantial exclusion of other specimen components, wherein the receptor is present in malignant tumor cells of epithelial cell origin;

e. differentially analyzing amounts of said labeled malignant cells and said labeled clusters of malignant cells in step d) over time, a change in the numerical proportions of said labeled malignant cells and said labeled clusters of malignant cells indicating a change of malignancy.

10. The method of claim 9, wherein said is blood sample is whole blood sample.

11. The method of claim 10, wherein after said blood sample is obtained, it is contacted with an agent capable of stabilizing said blood sample.

12. The method of claim 9, wherein after the step of preparing said magnetically-labeled sample, said sample is subjected to a high gradient magnetic field to produce a separated magnetically-labeled fraction which is enriched for said intact malignant cells and said clusters of malignant cells.

13. The method of claim 9, wherein said analysis is selected from the group consisting of: multiparameter flow cytometry, immunofluorescent microscopy, laser, scanning cytometry, bright field base image analysis, capillary volumetry, spectral imaging analysis, manual cell analysis, and automated cell analysis.

14. A kit for assaying a blood sample suspected of containing intact malignant cancer cells of epithelial cell origin for the presence of malignant cells, cell fragments derived from malignant cells and cellular debris derived from malignant cells, comprising:

a. coated colloidal magnetic nanoparticles comprising:
   i. a magnetic core material having a size range between 90 to 150 nm;
   ii. a protein base coating comprising bovine serum albumin applied using high temperature; and
   iii. an antibody that binds specifically to an epitope present in each of said intact malignant cells, said cell fragments and said cellular debris, wherein said antibody is coupled to said protein base coating on the colloidal magnetic nanoparticle;

b. at least one antibody having binding specificity for a receptor of said malignant cell, said cell fragments and said cellular debris, and wherein the receptor is present in malignant tumor cells of epithelial cell origin; and c. an agent capable of staining further morphological features of said malignant cells, said cell fragments and said cellular debris.

15. The kit of claim 14, further comprising a panel of antibodies each specific for a different characteristic determinant.

16. The kit of claim 14, further comprising a specific agent capable of labeling non-target entities.

* * * * *